(12) United States Patent
Wakabayashi et al.

(10) Patent No.: US 6,180,647 B1
(45) Date of Patent: *Jan. 30, 2001

(54) SUBSTITUTED BENZOLACTAM COMPOUNDS AS SUBSTANCE P ANTAGONISTS

(75) Inventors: Hiroaki Wakabayashi, Kariya; Masaya Ikunaka, Aichi-ken, both of (JP)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/983,004
(22) PCT Filed: May 9, 1996
(86) PCT No.: PCT/IB96/00434
§ 371 Date: Mar. 25, 1998
§ 102(e) Date: Mar. 25, 1998
(87) PCT Pub. No.: WO97/03066
PCT Pub. Date: Jan. 30, 1997

(30) Foreign Application Priority Data

Jul. 7, 1995 (WO) ................................ PCT/JP95/01359

(51) Int. Cl.⁷ .................... A61K 31/4709; C07D 401/12
(52) U.S. Cl. ........................................ 514/312; 546/158

(58) Field of Search ............................... 546/158; 514/312

(56) References Cited

U.S. PATENT DOCUMENTS

| 4,680,283 | 7/1987 | Veber et al. .................. 514/17 |
| 5,310,743 | 5/1994 | Schilling et al. . |

FOREIGN PATENT DOCUMENTS

| 0532456 | 3/1993 | (EP) . |
| 9005729 | 5/1990 | (WO) . |
| 9413663 | 6/1994 | (WO) . |

*Primary Examiner*—Patricia L. Morris
(74) *Attorney, Agent, or Firm*—Peter C. Richardson; Gregg C. Benson; Mervin E. Brokke

(57) ABSTRACT

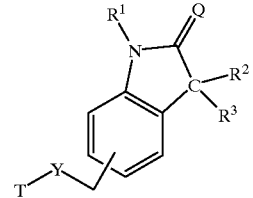

Compounds of the formula are effective for the treatment of conditions in mammals which require inhibition of the action of substance P.

6 Claims, No Drawings

SUBSTITUTED BENZOLACTAM COMPOUNDS AS SUBSTANCE P ANTAGONISTS

TECHNICAL FIELD

This invention relates to substituted benzolactam and cyclicthioamide compounds of interest to those in the field of medical chemistry and chemotherapy. More particularly, it is concerned with a series of substituted benzolactam and cyclicthioamide compounds, including their pharmaceutically acceptable salts, which are of special value in view of their ability to antagonize substance P. These compounds are of use in treating gastrointestinal disorders, central nervous system (CNS) disorders, inflammatory diseases, emesis, urinary incontinence, pain, migraine, angiogensis or the like, especially CNS disorders in a mammalian subject, especially humans.

BACKGROUND ART

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachyknin antagonists are useful for the treatment of allergic conditions, immunoregulation, vasodilation, bronchospasm, reflex or neuronal control of the viscera and senile dementia of the Alzheimer type, emesis, sunburn and Helicobacter pylori infection.

International Publication No. WO 94/13663 discloses a wide variety of azaheterocyclic compounds as tachykinin antagonists such as substance P antagonists. However, none of the compounds specifically disclosed in the references have good activity against CNS disorders with decreased adverse effects (e.g., $Ca^{2+}$ channel binding affinity).

BRIEF DESCRIPTION OF THE INVENTION

The present invention provides substituted benzolactam and cyclicthioamide compounds of the following chemical formula (I):

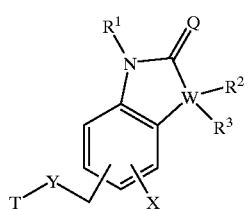

(I)

and its pharmaceutically acceptable salts, wherein

W is methylene, ethylene, propylene, vinylene, —$CH_2$—O—, —O—$CH_2$—, —$CH_2$—S— or —S—$CH_2$—;

$R^1$, $R^2$ and $R^3$ are independently hydrogen, $C_1$–$C_3$ alkyl, $C_1$–$C_3$ alkoxy or halo $C_1$–$C_3$ alkyl, provided that when W is methylene, both $R^2$ and $R^3$ are not hydrogen;

X is halo, $C_1$–$C_3$ alkoxy, $C_1$–$C_3$ alkyl, halo $C_1$–$C_3$ alkoxy or $C_1$–$C_3$ alkenyl;

Y is imino or oxy;

Q is oxygen or sulfur; and

T is (2S,3S)-2-diphenylmethylquinuclidin-3-yl, (2S,3S)-2-phenylpiperidin-3-yl or (2S,3S)-2-diphenylmethyl-1-azanorbornan-3-yl.

Also, this invention includes an intermediate compound useful for preparation of the compounds of formula (I), which is (2S,3S)-3-amino-1-(tert-butoxycarbonyl)-2-phenylpiperidine.

The compounds of the present invention of formula (I) exhibit good antagonist activity toward Substance P, particularly good activity against CNS disorders with decreased side effects (e.g., $Ca^{2+}$ channel affinity), and are thus useful for treatment of a gastrointestinal disorder, a central nervous system disorder, an inflammatory disease, emesis, urinary incontinence, pain, migraine or angiogensis in a mammalian subject, especially human.

Accordingly, the present invention provides a pharmaceutical composition for the treatment of a gastrointestinal disorder, a central nervous system disorder, an inflammatory disease, emesis, urinary incontinence, pain, migraine or angiogensis in a mammalian subject, which comprises a therapeutically effective amount of a compound of the formula (I) together with a pharmaceutically acceptable carrier.

DETAILED DESCRIPTION OF THE INVENTION

In this specification, the term "halo $C_1$–$C_3$ alkyl" is used herein to mean a $C_1$–$C_3$ alkyl radical substituted with one or more halogens (e.g., Cl, F, I or Br) including, but not limited to, chloromethyl, trifluoromethyl, 2,2,2-trichloroethyl and the like; and the term "halo $C_1$–$C_3$ alkoxy" is used herein to mean a $C_1$–$C_3$ alkoxy radical substituted with one or more halogens (e.g., Cl, F, I or Br) including, but not limited to, difluoromethoxy, trifluoromethoxy, 2,2,2-trifluoroethoxy and the like.

A preferred group of compounds of this invention includes the compounds of formula (I) wherein $R^1$, $R^2$ and $R^3$ are independently hydrogen, $C_1$–$C_3$ alkyl, $C_1$–$C_3$ alkoxy or halo $C_1$–$C_3$ alkyl, provided that when W is methylene, both $R^2$ and $R^3$ are not hydrogen; X is $C_1$–$C_3$ alkoxy or halo $C_1$–$C_3$ alkoxy; Y is imino; and T is (2S,3s)-2-diphenylmethylquinuclidin-3-yl or (2S,3S)-2-phenylpiperidin-3-yl.

A particularly preferred group of compounds of the invention includes the compounds of formula (I), wherein $R^1$ is methyl, isopropyl, methoxy or 2,2,2-trifuluoroethyl; $R^2$ and $R^3$ are independently hydrogen, methyl or trifluoromethyl, provided that when W is methylene, both $R^2$ and $R^3$ are not hydrogen; and X is methoxy, isopropoxy, difluoromethoxy or trifuluoromethylmethoxy. When W is methylene, T—Y—$CH_2$— and X are preferably at 5- or 6-position on the benzolactam ring. When W is ethylene or vinylene, T—Y—$CH_2$— and X are preferably at 6- or 7- position on the benzolactam ring. When W is —$CH_2$—O—, —O—$CH_2$—, —$CH_2$—S— or —S—$CH_2$—, X and T—Y—$CH_2$— are preferably at 6- or 7- position on the benzoxadine and benzothiadine ring. When W is propylene, X and T—Y—CH$_2$— are preferably 7- or 8- position on the benzazepin ring, respectively.

Preferred individual compounds of this invention are the following:

(2S,3S)-3-(6-methoxy-1,3,3-trimethyloxindol-5-yl) methylamino-2-phenylpiperidine or its salts;

(2S,3S)-3-(6-methoxy-1-methyl-2-oxo-1,2,3,4-tetrahydroquinolin-7-yl)methylamino-2-phenylpiperidine or its salts;

(2S,3S)-3-(6-isopropoxy-1-methyl-2-oxo-1,2,3,4-tetrahydroquinolin-7-yl)methylamino-2-phenylpiperidine or its salts;

(2S,3S)-3-(1-isopropyl-6-methoxy-2-oxo-1,2,3,4-tetrahydroquinolin-7-yl)methylamino-2-phenylpiperidine or its salts;

(2S,3S)-3-[(6-methoxy-1-methyl-2-thioxo-1,2,3,4-tetrahydroquinolin-7-yl)methyl]amino-2-phenylpiperidine dihydrochloride or its salts;

(2S,3S)-3-[(7-methoxy-1-methyl-2-oxo-1,2,3,4-tetrahydroquinolin-6-yl)methyl]amino-2-phenylpiperidine dihydrochloride or its salts; and (2S,3S)-3-[(6-methoxy-1-methyl-2-oxo-4H-3,1-benzothiazin-7-yl)methyl]amino-2-phenylpiperidine dihydrochloride or its salts.

Particularly preferred individual compounds of this invention are the following:

(2S,3S)-2-diphenylmethyl-3-(6-methoxy-1,3,3-trimethyloxindol-5-yl)methylamino-1-azabicyclo[2.2.2] octane or its salts;

(2S,3S)-2-diphenylmethyl-3-(6-methoxy-1-methyl-2-oxo-1,2,3,4-tetrahydroquinolin-7-yl)methylamino-1-azabicyclo[2.2.2]octane or its salts;

(2S,3S)-2-diphenylmethyl-3-(6-methoxy-1-methyl-2-oxo-1,2-dihydroquinolin-7-yl)methylamino-1-azabicyclo [2.2.2]octane or its salts;

(2S,3S)-3-[(6-methoxy-1-methyl-2-thioxo-1,2,3,4-tetrahydroquinolin-7-yl)methyl]amino-2-phenylpiperidine dihydrochloride or its salts; and (2S,3S)-3-[(6-methoxy-1-methyl-2-oxo-4H-3, 1-benzothiazin-7-yl)methyl]amino-2-phenylpiperidine dihydrochloride or its salts.

General Synthesis

The compounds of the formula (1) of this invention may be prepared as described in the following reaction schemes.

Unless otherwise indicated, in the reaction schemes that follow, R$^1$, R$^2$, R$^3$, X, Y, Z, W, Q and T are defined as above.

Scheme A-I

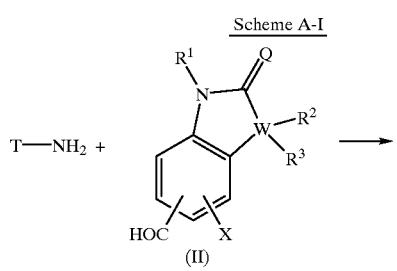

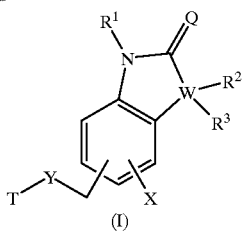

Scheme A-I illustrates a method for preparing compounds of the formula (I) by reductive amination of a compound of the formula (II) with a compound of the formula: T—NH$_2$ (Y=NH). The reduction can be carried out by catalytic hydrogenation, or with several hydride reagents in a reaction-inert solvent. The catalytic hydrogenation may be carried out in the presence of a metal catalyst such as palladium or Raney nickel. Suitable hydride reagents include borohydrides such as sodium borohydride (NaBH$_4$), sodium cyanoborohydride (NaBH$_3$CN) and sodium triacetoxyborohydride (NaB(OAc)$_3$H), boranes, aluminum-based reagents and trialkylsilanes. Suitable solvents include polar solvents such as methanol, ethanol, methylene chloride, tetrahydrofuran (THF), dioxane and ethylacteate. This reaction is typically carried out at a temperature from −78° C. to reflux temperature of the solvent, preferably from 0° C. to 25° C. for 5 minutes to 48 hours, preferably from 0.5 to 12 hours.

Alternatively, the compounds of the formula (I) of this invention may be prepared as shown in the following scheme A-II.

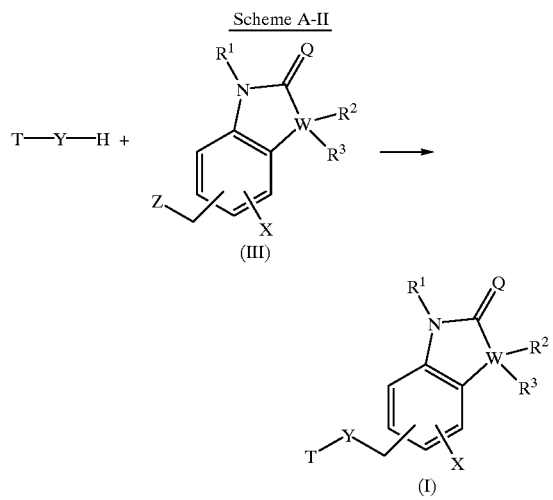

(wherein Z is a leaving group such as halo or sulfonate including tosylate or mesylate)

Referring to Scheme A-II, the compounds of the formula (I) of this invention may be prepared by a reaction of a compound of the formula (III) with a compound of the formula: T—Y—H. When Y is NH, the compound (III) may be treated with T—NH$_2$ in the presence of a base (e.g., K$_2$CO$_3$ or Na$_2$CO$_3$) in a polar solvent (e.g., methanol, ethanol, isopropylalcohol, THF, dioxane, dimethylformamide (DMF) or dimethylsulfoxide (DMSO)). When Y is O, the compound (III) may be treated with T—OH in the presence of a base (e.g., NaH or KH) in a polar solvent (e.g., THF, dioxane, DMF or DMSO). This reaction is typically carried out at a temperature from −78° C. to reflux temperature of the solvent, preferably from 0° C. to 25° C. for 5 minutes to 48 hours, preferably from 0.5 to 12 hours.

The compounds (III) may be prepared by reduction of an aldehyde of the formula (II), followed by conversion of a hydroxy group of the resultant compound into a leaving group, Z. Reduction of the aldehyde (II) may be accomplished using a variety of reducing agents in a reaction-inert solvent. Suitable reducing agent/solvent systems include sodium tetrahydroborate ($NaBH_4$) in methanol or ethanol; lithium tetrahydroborate ($LiBH_4$) in THF or diethyl ether; lithium tetrahydroaluminium ($LiAlH_4$), lithium triethoxyhydroaluminium ($LiAl(OEt)_3H$) lithium tert-buthoxyhydroaluminium ($LiAl(OBut)_3H$) or aluminium trihydride ($AlH_3$) in THF or diethyl ether; and iso-buthyl aluminium hydride(i-$BuAlH_2$) or diisopropyl aluminum hydride (DIBAL-H) in dichloromethane, THF or n-hexane. This reaction is generally carried out at a temperature from −20° C. to 25° C. for 5 minutes to 12 hours. Then, the hydroxy group of the resultant compound is converted to a leaving group, Z (e.g., halo such as chloro, bromo, iodo or fluoro, or sulfonate including tosylate or mesylate). Conversion of the hydroxy group into the leaving group, Z may be accomplished according to methods known to those skilled in the art. For example, when Z is sulfonate such as tosylate or mesylate, the hydroxy compound is reacted with sulfonate in the presence of pyridine or triethylamine in dichloromethane. When Z is halo such as chloro or bromo, the hydroxy compound may be treated with $SOX_2$ (X is Cl or Br) in the presence of pyridine.

The compounds of the formula (II) can be prepared as illustrated in the following scheme B.

Soc. Jpn. 64, 1118 (1991). The reduction as used herein may be performed in the presence of diisopropyl aluminiumhydride (DIBAL-H) in dichloromethane or Raney nickel in formic acid.

In addition, the compound (II) wherein W is vinylene can be prepared by dehydrogenation of the formula (II) wherein W is ethylene in a suitable solvent such as dioxane.

The starting materials of the formula (IV) are known compounds which are commercially available, or can be prepared by known methods. For example, compounds of the formula (IV) wherein $R^1$ is alkyl can be prepared by N-alkylation of the corresponding compounds (IV) wherein $R^1$ is hydrogen, in the presence of a base (e.g., NaH or KH) in a suitable solvent (e.g., DMSO, DMF and THF). Compounds of the formula (IV) wherein $R^2$ or $R^3$ is not hydrogen, can be also prepared from the corresponding compounds (IV) wherein $R^2$ or $R^3$ is hydrogen, using similar techniques as described above. Compounds (IV) can be also prepared by other methods as described in European Patent No. 385662 and C. Crestini. et. al., *Synth. Commun.* 24 2853 (1994) or G. W. Rewcastle et. al., *J. Med Chem*, 37, 2033 (1994). Compound (IV) wherein Q is S, can be prepared by thionation of the corresponding compound (IV) wherein Q is O. Suitable thionation agents are Lawesson reagent (*Tetrahedron*. 41, 5061 (1985)) and $P_4S_{10}$ (*Chem. Pharm. Bull.* 10, 647 (1962)).

Alternatively, compounds of the formula (I) wherein T is 2-phenylpireridinyl and Y is NH, may be prepared as shown in the following Scheme A-III.

Scheme B

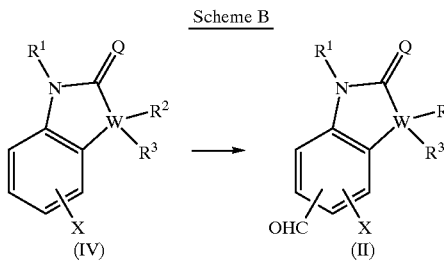

The compounds of the formula (II) may be prepared by direct or indirect formylation of a compound of the formula (IV). Any formylation methods known to those skilled in the art may be used, to introduce a formyl group into a benzene ring. For example, direct formylation may be accomplished by contacting the compound (IV) with a suitable formylating agent in the presence of a suitable catalyst. Suitable formylating agent/catalyst systems include dichloromethyl methyl ether/titanium (IV) chloride ($Cl_2CHOCH_3/TiCl_4$), trifluoroacetic acid ($CF_3CO_2H$) /hexamethylenetetramine (modified Duff's conditions) and phosphoryl trichloride ($POCl_3$)/DMF (Vilsmeier's conditions). Indirect formylation may be achieved by halogenating the compound (IV), displacing the halogen atom introduced with a cyano group, and then subjecting the resultant cyano-substituted compound to reduction. The halogenation as used herein may be carried out according to the procedure reported in G. A. Olah et., al. *J. Org. Chem*, 58, 3194 (1993). The displacement of the halogen atom with a cyano group may be performed according to the methods reported in D. M. Tschaem et. al., *Synth Commun.* 24, 887 (1994), K. Takagi et. al., 64 *Bull Chem.*

Scheme A-III

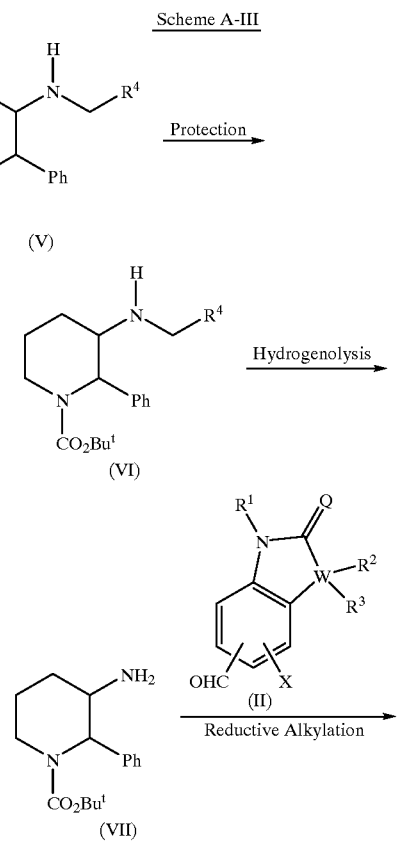

-continued

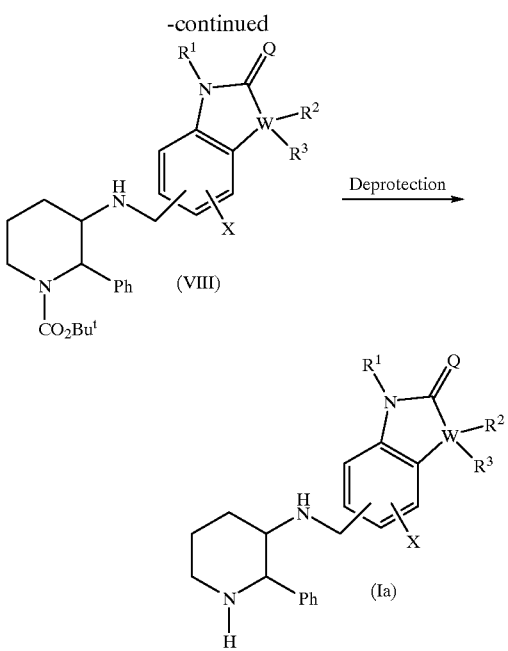

Scheme A-III illustrates the preparation of compounds of the formula (Ia) (corresponding to Compound (I) wherein T is 2-phenylpiperidinyl and Y is NH).

Referring to Scheme A-III, N-protection of a compound of the formula (V) ($R^4$ is phenyl or the like) may be carried out by treatment with (t-BuOCO)$_2$O (Boc$_2$O) in the presence of a base such as sodium bicarbonate (NaHCO$_3$) or triethylamine (Et$_3$N) to obtain a compound of the formula (VI). Compound (VI) is subjected to hydrogenolysis to obtain a compound of the formula (VII) (wherein $R^5$ is phenyl; and $R^6$ is t-butoxycarbonyl. An alternative route for N-protection of a compound of the formula (V) may be carried out by treatment with carbobenzoxy chloride (Cbz-Cl) in the presence of a base such as sodium bicarbonate (NaHCO$_3$) or triethylamine (Et$_3$N), wherein $R^5$ is phenyl; and $R^6$ is benzyloxycarbonyl. The hydrogenolysis may be carried out by treatment with H$_2$ or ammonium formate (HCO$_2$NH$_4$) in the presence of a metal catalyst such as a palladium on charcoal (e.g. 20% palladium on charcole) in a suitable solvent. Then, the compound (VII) is subjected to the reductive amination as described in Scheme A-I. The compound (VIII) may be converted into a compound of the formula (Ia) by treatment with acid catalyst such as hydrochloride (HCl) in methanol, conc.HCl in ethylacetate or CF$_3$CO$_2$H in dichloroethane.

The compounds of formula (I), and the intermediates shown in the above reaction schemes can be isolated and purified by conventional procedures, such as recrystallization or chromatographic separation.

As the compounds of formula (I) of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the compounds of formula (I) of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically acceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, ptoluenesulfonate and pamoate (i.e., 1.1'-methylene-bis-(2-hydroxy-3-naphthoate))salts.

The compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic derivatives. These particular non-toxic base salts include those derived form such pharmaceutically acceptable cations as sodium, potassium, calcium and magnesium, etc. These salts can easily be prepared by treating the aforementioned acidic compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active compounds of the present invention exhibit significant substance P receptor-binding activity and therefore, are of value in the treatment of a wide variety of clinical conditions which are characterized by the presence of an excess of said substance P activity. Such conditions include gastrointestinal disorders, central nervous system disorders, inflammatory diseases, emesis, urinary incontinence, pain, migraine or angiogensis in a mammalian subject, especially humans.

The active compounds of the formula (I) of this invention can be administered via either the oral, parenteral or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 2 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive ligands. The substance P antagonist activity of the herein described compounds is evaluated by using the standard assay procedure described by D. G. Payan et al., as reported in the *The Journal of Immunology*, 133, 3260 (1984). This method essentially involves determining the concentration of the individual compound required to reduce by 50% the amount of radiolabelled substance P ligands at their receptor sites in said isolated cow tissues or IM-9 cells, thereby affording characteristic $IC_{50}$ values for each compound tested. More specifically, inhibition of [$^3$H] SP binding to human IM-9 cells by compounds are determined in assay buffer (50 mM Tris-HCl (pH 7.4), 1 mM $MnCl_2$, 0.02% bovine serum albumin, bacitracin (40 $\mu$g/ml), leupeptin (4 $\mu$g/ml), chymostatin (2 $\mu$g/ml) and phosphoramidon (30 $\mu$g/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenimine for 2 hours). Nonspecific binding is defined as the radioactivity remaining in the presence of 1 $\mu$M SP. The filters are placed into tubes and counted using liquid scintillation counter.

The adverse effect on $Ca^{2+}$ channel binding affinity is determined by verapamil binding study in rat heart membrane preparation. More specifically, verapamil binding study is performed as previously described by Reynolds et al., (*J. Pharmacol. Exp. Ther.* 237, 731, 1986). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 $\mu$M methoxyverapamil.

The activity of the compounds of this invention against CNS disorder is determined by [$Sar^9$, $Met(O_2)^{11}$]substance P-induced tapping test in gerbils. More specifically, gerbils are lightly anesthetized with ether and the skull surface is exposed. [$Sar^9$, $Met(O_2)^{11}$]substance P or vehicle (5 $\mu$l) are administered directly into the lateral ventricles via a 25 gauge needle inserted 3.5 mm below lambda. Following injection, gerbils are placed in 2 l beaker individually and monitored for repetitive hind paw tapping. Some compounds prepared in the following Examples were tested in accordance with these testing methods. As a result, it was found that the compounds of the present inventions have good agonist activity toward Substance P, particularly good activity against CNS disorders with decreased side effects.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz for $^1$H, 67.5 MHz for $^{13}$C) unless otherwise indicated and peak positions are expressed in parts per million (ppm) downfield from tetramethylsilane. The peak shapes are denoted as follows: s, singlet; d, doublet; t, triplet; m, multiplet; br, broad.

Example 1

Preparation of (2S,3S)-2-Diphenylmethyl-3-(6-methoxy-1,3,3-trimethyloxindol-5-yl)methylamino-1-azabicyclo[2.2.2]octane monobesylate (Compound 6)

(i) 6-Methoxyoxindole (Compound 1)

This compound was prepared according to Quallich and Morrissey's procedures (Synthesis 51(1993)).

(ii) 6-Methoxy-1,3,3-trimethyloxindole (Compound 2)

To a stirred and ice-cooled suspension of NaH [60% in oil, 3.93 g, 98.1 mmol; washed with n-pentane (15.0 ml) three times prior to use] in dry DMF (50.0 ml) was added compound 1 (4.00 g, 24.5 mmol) portionwise. To this grey suspension was added neat MeI (6.11 ml, d2.280, 98.1 mmol) dropwise with ice-cooling. The mixture was stirred at room temperature for 45 minutes. After the mixture was ice-cooled, $H_2O$ (90.0 ml) was added. The mixture was extracted with ethyl acetate/toluene (AcOEt/PhMe) (2:1; 70.0 ml×3). The combined AcOEt/PhMe (2:1) extracts were washed with $Na_2S_2O_3$ aq. (×1), $H_2O$ (×1), and sat. NaCl aq. (×1), dried ($MgSO_4$), treated with activated charcoal, and concentrated in vacuo to give a red syrup (5.18 g). This was purified by medium pressure silica gel chromatography [Merck Kieselgel 60, 100 g; n-hexane-AcOEt (20:1-15:1-10:1)] to give compound 2 (4.74 g, 94.2%) as white crystals.

$^1$H-NMR (270 MHz) δ ($CDCl_3$) 7.09 (d, J=8.1 Hz, 1H), 6.56 (dd, J=8.1, 2.2 Hz, 1H), 6.44 (d, J=2.2 Hz,. 1H), 3.83 (s, 3H), 3.19 (s, 3H), 1.34 (s, 6H) ppm.

(iii) 5-Formyl-6-methoxy-1,3,3-trimethyloxindole (Compound 3)

The title compound 3 was prepared from compound 2 by applying the method reported by Rieche, A., Gross, H., and Höft, E. (*Org. Synth. Coll.* Vol., V, 49).

To a stirred and ice-cooled solution of compound 2 (1.00 g, 4.87 mmol) in dry $CH_2Cl_2$ (30.0 ml) was added neat $TiCl_4$ (1.60 ml, d1.730, 14.6 mmol) followed by dichloromethyl methyl ether ($Cl_2CHOMe$) (0.66 ml, d1.271, 7.31 mmol). After the addition was complete, the resultant dark green mixture was stirred at room temperature for 45 minutes. $H_2O$ (60.0 ml) was added with ice-cooling, and the layers were separated. The aqueous layer was extracted with $CH_2Cl_2$ (20.0 ml×3). The combined $CH_2Cl_2$ layer and extracts were washed with sat. NaCl aq. (×1), sat. $NaHCO_3$ aq. (×1), and sat. NaCl aq., dried ($MgSO_4$), treated with activated charcoal, and concentrated in vacuo to give a white solid. This was recrystallized from i-PrOH/i-$Pr_2O$ to give compound 3 (1.07 g, 94.1%).

mp 190.8–193.2° C.; IR $v_{max}$ (nujol) 1718(s), 1709(s) cm$^{-1}$; $^1$H-NMR (270 MHz) δ ($CDCl_3$) 10.37 (s, 1H), 7.70 (s,1H), 6.43 (s,1H), 3.99 (s, 3H), 3.27 (s, 3H), 1.36 (s, 6H) ppm. Anal. % Calc for $C_{13}H_{15}NO_3$: C; 66.94, H; 6.48, N; 6.00. Found: C; 66.84, H; 6.47, N; 6.04.

(iv) (2S,3S)-3-Amino-2-diphenylmethyl-1-azabicyclo[2.2.2]octane (Compound 4)

This compound was prepared according to the procedure (*J. Med. Chem.*, 18, 587(1975))

(v)(2S,3S)-2-Diphenylmethyl-3-(6-methoxy-1,3,3-trimethyloxindol-5-yl)methylamino-1-azabicyclo[2.2.2]octane (Compound 5)

Reductive alkylation of compound 4 with compound 3 was carried out according to the procedures reported by Abdel-Magid, A. F., Maryanoff, C. A., and Carson, K. G. (*Tetrahedron Lett.*, 31, 5595 (1990)).

To a stirred solution of compound 4 (1.28 g, 4.36 mmol), compound 3 (1.07 g, 4.58 mmol) and AcOH (0.50 ml, d1.049, 8.72 mmol) in dry $CH_2Cl_2$ was added sodium triacetoxyborohydride ($NaB(OAc)_3H$) (1.39 g, 6.54 mmol) at room temperature. The mixture was stirred at room temperature for 3.5 hours. The mixture was basified with 10% NaOH aq. (ca. 10.0 ml), and the layers were separated. The aqueous layer was extracted with $CH_2Cl_2$ (8.0 ml×3). The combined $CH_2Cl_2$ layer and extracts were washed with sat. NaCl aq. (×1), dried ($K_2CO_3$), and concentrated in vacuo to give a colorless glass. This was recrystallized from i-PrOH/i-$Pr_2O$ to give compound 5 (1.89 g, 85.0%) as a white powder.

mp 184.7–189.1° C.; IR $v_{max}$ (nujol) 1710(s), 1620(m), 1600(w), 1497(m), 1125(m), 1062(m), 830(w), 800(w), 756 (w), 744(w), 706(w), 693(m) cm$^{-1}$; $^1$H-NMR (270 MHz) a ($CDCl_3$) 7.41-7.30 (m, 2H), 7.32-7.21 (m, 2H), 7.24-7.12 (m, 5H), 6.54 (s, 1H), 6.28 (s, 1H), 4.49 (d, J=12.1 Hz, 1H), 3.70 (dd, J=12.1, 8.1Hz, 1H), 3.61 (s, 3H), 3.61 (d, J=12.6 Hz), 3.27-3.06 (m, 1H), 3.19 (s, 3H), 3.14 (d, J=12.6 Hz, 1H), 2.94 (ddd, J=3.9, 3.9, 3.9 Hz, 1H), 2.77 (br.dd, J=7.5, 7.5 Hz, 2H), 2.60 (br.dd, J=11.5, 115 Hz), 2.13-2.03 (m, 1H), 2.02-1.86 (m, 1H), 1.75-1.40 (m, 3H), 1.40-1.16 (m,1H), 1.32 (s, 3H), 1.31 (s, 3H) ppm. Anal. % Calc for $C_{33}H_{39}N_3O_2$: C; 77.77, H; 7.71, N; 8.24. Found: C; 77.62, H; 7.81, N; 8.15.

(vi) (2S,3S)-2-Diphenylmethyl-3-(6-methoxy-1,3,3-trimethyloxindol-5-yl)methylamino-1-azabicyclo[2.2.2]octane monobesylate (Compound 6)

After compound 5 (0.200 g, 0.392 mmol) was dissolved in acetone with warming, to this solution was added a solution of $PhSO_3H$ $H_2O$ (69.1 mg, 0.392 mmol) in acetone. When this mixture was allowed to cool to room temperature, precipitation of white solids took place. After the mixture was left to stand in a refrigerator at 4° C. overnight, the crystals precipitated were collected by filtration, washed with ice-chilled acetone (×2), and dried in vacuo at room temperature to give compound 6 (0.198 g, 75.7%) as a white powder.

mp 242.7–247.7° C. (decomp.); IR $v_{max}$ (nujol) 1713(s), 1699(s), 1620(s), 1600(m), 1500(s), 1220(s), 1175(s), 1124 (s), 853(m), 820(m), 755(s), 725(s), 725(s), 707(s), 698(s) cm$^{-1}$; $^1$H-NMR (270 MHz) δ ($CDCl_3$) 7.76-7.63 (m, 2H), 7.43-7.20 (m, 9H), 7.27-7.12 (m, 3H), 7.13-7.01 (m, 1H), 6.52 (s, 1H), 6.30 (s, 1H), 4.54 (d, J=12.1 Hz, 1H), 4.60-4.45 (m, 1H), 3.70-3.40 (m, 4H), 3.60 (s, 3H), 3.53 (d, J=12.3 Hz, 1H), 3.32-3.20 (m, 1H), 3.20 (s, 3H), 3.16 (d, J=12.3 Hz, 1H), 2.46-2.35 (m, 1H), 2.35-2.18 (m, 1H), 2.13-1.95 (m, 2H), 2.05-1.65 (m, 2H), 1.65-1.45 (m, 1H), 1.31 (s, 6H) ppm. Anal. % Calc for $C_{39}H_{45}N_3O_5S$: C; 70.14, H; 6.79, N; 6.29. Found: C; 70.09, H; 6.88, N; 6.21.

Example 2

Preparation of (2S,3S)-3-(6-Methoxy-1,3,3-trimethyloxindol-5-yl)methylamino-2-phenylpiperidine dihydrochloride (Compound 13)

(i) (2S,3S)-3-(2-Methoxybenzyl)amino-2-phenylpiperidine (Compound 7)

This compound was prepared according to the procedures disclosed in WO-93- 01170.

(ii) (2S,3S)-1-tert-Butoxycarbonyl-3-(2-methoxybenzyl)amino-2-phenylpiperidine (Compound 8)

To a stirred and ice-cooled mixture of compound 7 (10.0 g, 27.1 mmol), 3.0M NaOH aq. (36.1 ml, 108.4 mmol) and tert-BuOH (15.0 ml) was added (tert-BuOCO)$_2$O (Boc$_2$O, 7.39 g, 33.8 mmol) in one portion. After stirring at room temperature overnight, the mixture was extracted with AcOEt (50 ml×3). The combined AcOEt extracts were washed with $H_2O$ (×3), and sat. NaCl (×1), dried ($Na_2SO_4$), and concentrated in vacuo to give compound 8 (11.27 g, quant.) as a pale yellow syrup.

IR $v_{max}$ (film) 3350(w), 1693(s), 1605(s), 1590(m), 1492 (s), 755(m) cm$^{-1}$; $^1$H-NMR (270 MHz) δ ($CDCl_3$) 7.58 (br.d, J=7.3 Hz, 2H), 7.36-7.16 (m, 5H), 6.89 (ddd, J=7.5, 7.5, 1.1 Hz, 1H), 6.81 (dd, J=8.4, 0.8 Hz, 1H), 5.47 (br.s, 1H), 3.96 (dm, J=13.4 Hz, 1H), 3.87 (d, J=13.6 Hz, 1H), 3.79 (d, J=13.6 Hz, 1H), 3.70 (s, 3H), 3.10-2.99 (m, 1H), 2.94 (dd, J=12.5, 3.4 Hz, 1H), 1.87-1.74 (m, 2H), 1.74-1.40 (m, 3H), 1.41 (s, 9H) ppm.

This was employed in the next step without further purification.

(iii) (2S,3S)-3-Amino-1-tert-butoxycarbonyl-2-phenylpiperidine (Compound 9)

A mixture of compound 8 (11.27 g), 20% Pd(OH)$_2$/C (Pearlman's catalyst, 3.10 g), and MeOH (90 ml) was stirred under an atmosphere of H$_2$ (balloon) at room temperature overnight. After an additional amount of 20% Pd(OH)$_2$/C (0.55 g) was added, the stirring was continued under an atmosphere of H$_2$ (balloon) at room temperature for three days. The catalyst was filtered off by the aid of celite, and washed with MeOH thoroughly. The combined MeOH filtrate and washings were concentrated in vacuo to give crude compound 9 (8.59 g, quant.).

This was dissolved in EtOH (20.0 ml), and then a warmed solution of fumaric acid (1.57 g, 13.5 mmol) in EtOH (20.0 ml)was added in one portion to this solution at room temperature. When the mixture was scratched with a spatula, there took place precipitation of white solids with ease. After the mixture was left to stand at 4° C. in a refrigerator overnight, the crystals precipitated were collected by filtration, washed with ice-chilled EtOH (×1), and dried in vacuo at 50° C. to give a first crop of (2S,3S)-3-amino-1-(tert-butoxycarbonyl)-2-phenylpiperidinesemifumaratecompound10(6.14 g, 67.8%) as white short needles. The combined filtrate and washing were concentrated in vacuo to give a residual solid (4.56 g), which was recrystallized from EtOH and i-Pr$_2$O to give a second crop of compound 10 (1.25 g, 13.7%).

mp 165.7–168.8° C.; Anal. % Calc for C$_{18}$H$_{26}$N$_2$O$_4$.0.4 H$_2$O: C; 63.29, H; 7.91, N; 8.20. Found: C; 63.64, H; 8.22, N; 7.79.

After a suspension of compound 10 (1.24 g, 3.71 mmol) in H$_2$0 was ice-cooled, 20% NaOH aq. was added until the mixture became basic. The mixture was then extracted with AcOEt (×3). The combined AcOEt extracts were washed with sat. NaCl aq. (×1), dried (Na$_2$SO$_4$), and concentrated in vacuo to give pure compound 9 (0.95 g, 93.1 %).

IR $\nu_{max}$ (film) 3370(w), 3310(w), 1695(s), 1682(s), 1807 (m), 1590(w, shoulder), 1494(s), 1250(s), 1180(s), 1150(s), 756(m), 703(s) cm$^{-1}$; $^1$H-NMR (270 MHz) δ (CDCl$_3$) 7.47-7.39 (m, 2H), 7.37-7.23 (m, 5H), 5.19 (br,d, J=6.2 Hz, 1H), 4.00 (dm, J=13.0 Hz, 1H), 3.25-3.05 (m, 2H), 1.94-1.83 (m, 1H), 1.83-1.56 (m, 4H), 1.36 (s, 9H), 1.32 (br.s, 2H) ppm.

(iv) (2S, 3S)-1-tert-Butoxycarbonyl-3-(6-methoxy-1,3,3-trimethyloxindol-5-Yl) methylamino-2-phenylpiperidine (Compound 11)

Reductive alkylation of compound 9 with compound 3 was carried out according to the procedures reported by Abdel-Magid, A. F., Maryanoff, C. A., and Carson, K. G. (*Tetrahedron Lett.*, 31, 5595 (1990)).

To a stirred and ice-cooled solution of compound 9 (0.504 g, 1.82 mmol) and compound 3 (0.468 g, 2.01 mmol) in dry CH$_2$Cl$_2$ (17.0 ml) was added NaB(OAc)$_3$H (0.579 g, 2.73 mmol) in one portion. After the mixture was stirred at room temperature for eight hours, NaB(OAc)$_3$H (0.30 g, 1.42 mmol) and AcOH (0.104 ml, d1.049, 1.82 mmol) were added, and the stirring was continued at room temperature for additional three nights. The mixture was basified to pH9–10 with 10% NaOH aq. (9.0 ml), and the layers were separated. The aqueous layer was extracted with CH$_2$Cl$_2$ (×3). The combined CH$_2$Cl$_2$ layer and extracts were washed with NaCl aq. (×1), dried (K$_2$CO$_3$), and concentrated in vacuo to give a colorless syrup (1.06 g). This was flash-chromatographed over silica gel (Merck Kieselgel 60, 30 g). Elution with CH$_2$Cl$_2$-MeOH (200:1-150:1-100:1) gave compound 11 (0.644 g, 71.9%) as a colorless syrup.

IR $\nu_{max}$ (film) 3345(w), 1715(s), 1695(s), 1681(s), 1625 (s), 1604(s), 1508(s), 886(m), 820(m), 732(s), 703(s) cm$^{-1}$; $^1$H-NMR (270 MHz) δ (CDCl$_3$) 7.60 (br.d, J=7.0 Hz, 2H), 7.38-7.23 (m, 3H), 7.00 (s, 1H), 6.36 (s, 1H), 5.57-5.45 (m, 1H), 4.03- 3.89 (m, 1H), 3.84 (d, J=12.8 Hz, 1H), 3.78 (d, J=12.8 Hz, 1H), 3.74 (s,3H), 3.20 (s, 3H), 3.11-2.90 (m, 2H), 1.90-1.74 (m,2H), 1.74-1.45 (m, 3H), 1.41 (s, 9H), 1.32 (s, 3H), 1.31 (s, 3H) ppm.

(v)(2S,3S)-3-(6-Methoxy-1,3,3-trimethyloxindol-5-yl) methylamino-2-phenylpiperidine (Compound 12)

To a stirred and ice-cooled solution of compound 11 (0.64 g, 1.31 mmol) in AcOEt (5.0 ml) was added conc. HCl (2.0 ml) dropwise. The mixture was stirred at room temperature for 45 minutes. The mixture was ice-cooled, and then basified with 20% NaOH aq. (ca. 8.0 ml). The layers were separated, and the aqueous layer was extracted with AcOEt (×3). The combined AcOEt layer and extracts were washed with sat. NaCl aq. (×1), dried (K$_2$CO$_3$), and concentrated in vacuo to give compound 12 (0.48 g, 93.6%) as a colorless syrup.

IR $\nu_{max}$ (film) 3330(m), 1710(s), 1620(s), 1600(s), 1500 (s), 1250(s), 1125(s), 1060(m) cm$^{-1}$; $^1$H-NMR (270 MHz) δ (CDCl$_3$) 7.38-7.17 (m, 5H), 6.79 (s, 1H), 6.24 (s, 1H), 3.90 (d, J=2.4 Hz, 1H), 3.63 (d, J=13.7 Hz, 1H), 3.54 (s, 3H), 3.40 (d, J=13.7 Hz, 1H), 3.31-3.21 (m, 1H), 3.17 (s, 3H), 2.85 (ddd, J=2.4, 2.4, 2.4 Hz, 1H), 2.80 (ddd, J=12.6, 12.6, 3.1 Hz, 1H), 2.14 (dm, J=12.6 Hz, 1H), 1.93 (ddddd, J=12.6, 12.6, 12.6, 4.0, 4.0 Hz, 1H), 1.69 (br.s, 2H), 1.61 (dddd, J 12.6, 12.6, 3.7, 3.7 Hz, 1H), 1.42 (dm, J=12.6 Hz, 1H), 1.29 (s, 3H), 1.28 (s, 3H) ppm.

This was employed in the next salt formation step without further purification.

(vi) (2S,3S)-3-(6-Methoxy-1,3,3-trimethyloxindol-5-yl) methylamino-2-phenylpipendine dihydrochloride (Compound 13)

To a solution of compound 12 (0.48 g, 1.22 mmol) in MeOH (0.5 ml) was added an excess amount of Hydrogen Chloride, Methanol Reagent 10 (Tokyo Kasei, 6.0 ml). After the solvent MeOH was evaporated in vacuo, the residual solid was recrystallized from MeOH-Et$_2$O. The recrystallization mixture was left to stand at 4° C. in a refrigerator for three nights. The crystals precipitated were collected by filtration, washed with Et$_2$O (×2), and dried in vacuo at 50° C. to give compound 13 (0.401 g, 70.4%) as a white powder.

mp 223.7–239.7° C.; IR $\nu_{max}$ (nujol) 2900–2200(br., s), 1718(s), 1710(s), 1630(s), 1605(m), 1565(s), 1505(s), 1250 (s), 1180(s), 1129(s), 1060(m), 900(m), 850(m), 824(m), 765(m), 750(s), 692(s) cm$^{-1}$. Anal. % Calc for C$_{24}$H$_{33}$N$_3$O$_2$Cl$_2$: C; 61.80, H; 7.13, N; 9.01. Found: C; 61.67, H; 7.13, N; 9.00.

Example 3

Preparation of (2S,3S)-2-Diphenylmethyl-3-(6-methoxy-1-methyl-2-oxo-1,2,3,4-tetrahydroquinolin-7-yl) methylamino-1-azabicyclo[2.2.2]octane (Compound 17)

(i) 6-Methoxy-1-methyl-2-oxo-1,2-dihydroquinoline (Compound 14)

Preparation of compound 14 from 6-methoxyquinoline was carried out according to the procedures disclosed in EP 385662.

A mixture of 6-methoxyquinoline (16 g, 100 mmol) and dimethyl sulfate (13 g, 100 mmol) and in benzene (50 ml) was refluxed for 1 hr. After the reaction mixture was cooled down to room temperature, the orange solution was decanted off. The resulting salt was washed with benzene (30 ml×3). This salt was dissolved in H$_2$O (50 ml) and the solution was washed with benzene (30 ml). This solution and a solution of NaOH (12 g, 300 mmol) in $H_2O$ (50 mL) were added to a mixture of potassium ferricyanide (66 g, 200 mmol) in $H_2O$ and $CH_2Cl_2$ at room temperature over 15 min. The resulting mixture was stirred at room temperature for 15 hr. The organic layer was separated and the aqueous layer was extracted with $CH_2Cl_2$ (150 ml) three times. The combined extracts were dried over $Na_2SO_4$ and concentrated. The crude was purified by recrystallization from AcOEt-hexane to give compound 14 (12 g, 63 mmol, 63%) as a pale yellow crystal.

$^1$H-NMR (270 MHz) δ (CDCl$_3$) 7.70-6.70 (m, 5H), 3.88 (s, 3H), 3.72 (s, 3H) ppm.

(ii) 6-Methoxy-1-methyl-2-oxo-1,2,3,4-tetrahydroquinoline (Compound 15)

A mixture of compound 14 (3.0 g, 16 mmol), 10% Pd-C (0.7 g) and EtOH (20 ml) was heated in an autoclave at 100° C. under 50 atm of $H_2$ for 15hr. The catalyst was removed by filtration and the filtrate was concentrated in vacuo to give a crude solid. This was purified by recrystallization from MeOH to give compound 15 (1.8 g, 9.4 mmol, 53%) as a colorless crystal.

$^1$H-NMR (270 MHz) δ (CDCl$_3$) 6.96-6.68 (m, 3H), 3.79 (s, 3H), 3.33 (s, 3H), 2.95-2.56 (m, 4H) ppm.

(iii) 6-Methoxy-1-methyl-2-oxo-1,2,3,4-tetrahydroquinoline-7-carboxaldehyde (Compound 16)

This compound was prepared from compound 15 in the same manner of compound 3

$^1$H-NMR (270 MHz) δ (CDCl$_3$) 10.44 (s, 1H), 7.42 (s, 1H), 6.84 (s, 1H), 3.94 (s, 3H), 3.37 (s, 3H), 2.97 (t, 2H, J=7 Hz), 2.66 (t, 2H, J=7 Hz)

(iv) (2S,3S)-2-Diphenylmethyl-3-(6-methoxy-1-methyl-2-oxo-1,2,3,4-tetrahydroquinolin-7-yl)methylamino-1-azabicyclo[2.2.2]octane (Compound 17)

This compound was prepared from compound 16 and compound 4 in the same manner of compound 5 mp 136–139° C. $^1$H-NMR (270 MHz) a (CDCl$_3$) 7.38-6.43 (m, 12H), 4.47 (d, J=12 Hz, 1H), 3.75-2.55 (m, 13H), 3.54 (s, 3H), 3.27 (s, 3H), 2.16-1.20 (m, 4H) ppm. Anal. Calc for $C_{32}H_{37}N_3O_2.0.25H_2O$: C; 76.84%, H; 7.56%, N; 8.40%. Found: C; 76.81%, H; 7.45%, N. 8.41%.

Example 4

Preparation of (2S,3S)-2-Diphenylmethyl-3-(6-methoxy-1-methyl-2-oxo-1,2-dihydroquinolin-7-yl)methylamino-1-azabicyclo[2.2.2]octane (Compound 19)

(i) 6-Methoxy-1-methyl-2-oxo-1,2-dihydroquinoline-7-carboxaldehyde (Compound 18)

A mixture of compound 16 (2.0 g, 9.0 mmol), DDQ (9.0 g, 40 mmol) and dioxane (100 ml) was stirred and heated at 140° C. for two days. After the reaction mixture was cooled down to room temperature, the mixture was filtered and the filtrate was concentrated in vacuo. The residue was purified by a column chromatography on silicagel to give a pale yellow solid, which was recrystallized to give compound 18 (0.7 g, 31 mmol, 35%) as a pale yellow crystal.

$^1$H—NMR (270 MHz) δ (CDCl$_3$) 10.57 (s, 1H), 7.84 (s, 1H), 7.64 (d, J=10 Hz, 1H), 7.10 (s, 1H), 6.84 (d, J=10 Hz, 1H), 4.00 (s, 3H), 3.75 (s, 3H) ppm.

(ii) (2S,3S)-2-Diphenylmethyl-3-(6-methoxy-1-methyl-2-oxo-1,2-dihydroquinolin-7-yl)methylamino-1-azabicyclo[2.2.2]octane (Compound 19)

This compound was prepared from compound 18 and compound 4 in the same manner of compound 5 mp 125–128° C. $^1$H-NMR (270 MHz) δ (CDCl$_3$) 7.61-6.63 (m, 14H), 4.47 (d, J=12 Hz, 1H), 3.72-2.55 (m, 9H), 3.66 (s, 3H), 3.62 (s, 3H), 2.14-1.20 (m, 4H) ppm. *Anal. Calc for $C_{32}H_{35}N_3O_2.0.5H_2O$ 0.4(2-propanol)*: C; 75.71%, H; 7.50%, N; 7.98%. Found: C; 75.41%, H; 7.50%, N; 7.91%.

Example 5

Preparation of (2S,3S)-3-(6-methoxy-1-methyl-2-oxo-1,2,3,4-tetrahydroquinolin-7-yl)methylamino-2-phenylpiperidine dihydrochloride (Compound 21)

(i) (2S,3S)-2-Phenylpiperidin-3-amine dihydrochloride (Compound 20)

This compound was prepared according to the procedures disclosed in EP-558156.

(ii) (2S,3S)-3-(6-Methoxy-1-methyl-2-oxo-1,2,3,4-tetrahydroquinolin-7-yl)methylamino-2-phenylpiperidine dihydrochloride (Compound 21)

A mixture of compound 20 (250 mg, 1 mmol), compound 16 (220 mg, 1 mmol) and sodium triacetoxyborohydride (400 mg, 1.9 mmol) in $CH_2Cl_2$ (10 ml) was stirred at room temperature for 24 hr., quenched with $NaHCO_3$ aq, and extracted with $CH_2Cl_2$ three times. The combined extracts were dried over $Na_2SO_4$ and concentrated. The crude was purified by a column chromatography on silicagel to give a free base of compound 21. This was derived to dihydrochloride salt with HCl—MeOH, which was washed with IPA to give compound 21 (100 mg, 0.22 mmol, 22%) as a colorless crystal.

mp 265–268° C. IR $v_{max}$ (KBr) 3415, 2935, 1673, 1647, 1556, 1513, 1469, 1452, 1430, 1366, 1249, 1185, 1163, 1065, 1027 cm$^{-1}$. $^1$H—NMR (270 MHz) δ (free base; CDCl$_3$) 7.43-6.52 (m, 7H), 4.00-3.28 (m, 4H), 3.51 (s, 3H), 3.22 (s, 3H), 2.96-1.45 (m, 10H) ppm. Anal. Calc for $C_{23}H_{29}N_3O_2.2$ HCl.0.5 $H_2O$: C; 59.87%, H, 6.99%, N, 9.11%. Found: C; 59.82%, H; 7.37%, N, 9.23%.

The compound obtained was subjected to the IM-9 binding assay, the [Sar$^9$, Met($O_2$)$^{11}$]substance P-induced tapping test and the verapamil binding study as described before, with the results of less than 0.1 nM, 52% (% inhibition at 0.3 mg/kg scoring) and more than 3000 nM, respectively.

Example 6

Preparation of (2S,3S)-3-(6-Isopropoxy-1-methyl-2-oxo-1,2,3,4-tetrahydroquinolin-7-yl)methylamino-2-phenylpiperidine dihydrochloride (Compound 26)

(i) 6-Hydroxy-1-methyl-2-oxo-1,2,3,4-tetrahydroquinoline (Compound 22)

To a stirred solution of compound 15 (500 mg, 2.61 mmol) in $CH_2Cl_2$ (7 ml) was added $BBr_3$ (1.0M in $CH_2Cl_2$, 5.74 ml, 5.74 mmol) at room temperature, and stirred for 3h. The mixture was poured into ice water. The aqueous layer was extracted with AcOEt (×2). The combined organic layers were washed with sat. NaCl aq, dried (MgSO$_4$), filtered, and concentrated to give compound 22 (350 mg, 76%) as a colorless crystal.

$^1$H-NMR (270 MHz) δ (CDCl$_3$) 6.85 (1H, d, J=8.4 Hz), 6.75-6.70 (m, 2H), 3.34 (3H, s), 2.86 (2H, t, J=7.1 Hz), 2.63 (2H, t, J=7.1 Hz) ppm.

(ii) 6-Isopropoxy-1-methyl-2-oxo-1,2,3,4-tetrahydroquinoline (Compound 23)

To a stirred solution of compound 22 (350 mg, 1.98 mmol) and 2-iodopropane (0.590 ml, 5.93 mmol) in acetone (16 ml) was added $Cs_2CO_3$ (2.90 g, 8.91 mmol), and heated at 55° C. for 3h. The mixture was filtered over celite and washed with acetone. The filtrate was concentrated to give crude compound 23. This was diluted with AcOEt, washed with water and sat. NaCl aq, dried (MgSO$_4$), and concentrated. This was purified by SiO$_2$ chromatography to give compound 23 (382 mg, 88%) as a colorless oil.

$^1$H-NMR (270 MHz) δ (CDCl$_3$) 6.88 (1H, d, J 8.4 Hz), 6.80-6.70 (m, 2H), 4.49 (1H, hep, J=5.9 Hz), 3.33 (3H, s), 2.86 (2H, t, J=7.2 Hz), 2.66-2.59 (2H, m), 1.33 (6H, d, J=5.9 Hz) ppm.

(iii) 6-Isopropoxy-1-methyl-2-oxo-1,2,3,4-tetrahydroquinoline-7-carboxaldehyde (Compound 24)

To a stirred solution of compound 23 (382 mg, 1.74 mmol) in $CH_2Cl_2$ (10 ml) was added $TiCl_4$ (0.42 ml, 3.83 mmol) at −20° C. After the reaction mixture was stirred for 10 minutes, $Cl_2CHOMe$ (0.35 ml, 3.83 mmol) was added at −20° C.; and stirred for 2h. After $H_2O$ was added, the mixture was extracted with $CH_2Cl_2$ (×3). The combined extracts were dried ($MgSO_4$), filtered, and concentrated. The residue was purified by $SiO_2$ chromatography to give compound 24 (391 mg, 91%) as a slight yellow crystal.

$^1$H-NMR (270 MHz) δ (CDCl$_3$) 10.44 (1H, s), 7.41 (1H, s), 6.84 (1H, s), 4.65 (1H, hep, J=5.9 Hz), 3.36 (3H, s), 2.94 (2H, t, J=7.3 Hz), 2.66 (2H, t, J=7.3 Hz), 1.40 (6H, d, J=5.9 Hz) ppm.

(iv) (2S,3S)-1-tert-Butoxycarbonyl-3-(6-isopropoxy-1-methyl-2-oxo-1,2,3,4-tetrahydroquinolin-7-yl) methylamino-2-phenylpiperidine (Compound 25)

A mixture of compound 9 (436 mg, 1.58 mmol), compound 24 (390 mg, 1.58 mmol), sodium triacetoxyborohydride (670 mg, 3.16 mmol) and $CH_2Cl_2$ (8 ml) was stirred under nitrogen at room temperature for 2h. After $NaHCO_3$ aq. solution was added, the mixture was extracted with $CH_2Cl_2$ (×3). The combined extracts were dried ($MgSO_4$), filtered and concentrated. This was purified by $SiO_2$ chromatography to give compound 25 (698 mg, 87%) as a colorless oil.

$^1$H-NMR (270 MHz) δ (CDCl$_3$) 7.58 (2H, d, J=7.0 Hz), 7.37-7.22 (3H, m), 6.88 (1H, s), 6.64 (1H, s), 5.54-5.42 (1H, m), 4.45 (1H, hep, J=5.9 Hz), 4.02-3.78 (3H, m), 3.30 (3H,s), 3.12-2.92 (2H, m), 2.83 (2H, t, J=7.3 Hz), 2.61 (2H, t, J=7.3 Hz), 1.95-1.30 (4H, m), 1.40 (9H, s), 1.26 (3H, d, J=5.9 Hz), 1.24 (3H, d, J=5.9 Hz) ppm.

(v) (2S,3S)-3-(6-Isopropoxy-1-methyl-2-oxo-1,2,3,4-tetrahydro-quinolin-7-yl)methyl amino-2-phenylpiperidine dihydrochloride (Compound 26)

To a solution of compound 25 (312 mg, 0.615 mmol) in AcOEt (6 ml) was added an excess amount of Hydrogen Chloride, Methanol Reagent 10 (Tokyo Kasei, 3 ml). The mixture was stirred for 4 h and then evaporated in vacuo, the residual solid was recrystallized from MeOH-Et$_2$O to give compound 26 (140 mg, 47%) as a white crystal.

mp 249–251° C.; $^1$H-NMR (270 MHz) δ (free base; CDCl$_3$) 7.40-7.18 (5H, m), 6.63 (1H, s), 6.55 (1H, s), 4.31 (1H, hep, J=6.2 Hz), 3.89 (1H, d, J=2.2 Hz), 3.54 (1H, d, J=13.7 Hz), 3.41 (1H, d, J=13.7 Hz), 3.42-3.20 (1H, m), 3.20 (3H,s), 2.95-2.75 (4H, m), 2.64-2.55 (2H, m) 2.22-2.10 (1H, m), 1.98-1.82 (1H, m), 1.72-1.56 (1H, m), 1.52-1.39 (1H, m), 1.15 (3H, d, J=5.9 Hz), 1.12 (3H, d, J=5.9 Hz) ppm. IR $v_{max}$ (KBr) 3420, 2915, 2650, 2460, 1666, 1513, 1468, 1436, 1404, 1372, 1130, 964 cm$^{-1}$. Anal. calcd for $C_{25}H_{35}N_3O_2Cl_2$: C; 62.50%, H; 7.34%; N 8.75%; Found: C; 62.12%, H; 7.58%, N; 9.04%.

Example 7

Preparation of (2S,3S)-3-(6-Methoxy-1-methyl-2-oxo-1,2-dihydroquinolin-7-yl)methylamino-2-phenylpiperidine dihydrochloride (Compound 28)

(i)(2S,3)-1-tert-Butoxycarbonyl-3-(6-methoxy-1-methyl-2-oxo-1,2-dihydroquinolin-7-yl)methylamino-2-phenylpiperidine (Compound 27)

This compound was prepared from compound 18 and compound 9 in the same manner of compound 11.

$^1$H-NMR (270 MHz) δ (CDCl$_3$) 7.70-6.66 (9H, m), 5.52 (1H, br), 4.10-3.62 (3H, m), 3.77 (3H,s), 3.68 (3H,s), 3.30-2.92 (2H, m), 2.10-1.30 (4H, M), 1.40 (9H, s) ppm.

This was employed in the next step without further purification.

(ii) (2S,3S)-3-(6-Methoxy-1-methyl-2-oxo-1,2-dihydroquinolin-7-yl)methylamiano-2-phenylpiperidine dihydrochloride (Compound 28)

This compound was prepared from compound 27 in the same manner of compound 26.

mp 260–263° C. $^1$H-NMR (270 MHz) δ (free base; CDCl$_3$) 7.60-6.62 (9H, m), 3.95-2.75 (6H, m), 3.61 (3H,s), 3.54 (3H,s), 2.23-1.42 (4H, m) ppm. Anal. Calc for $C_{23}H_{27}N_3O_2$. 2 HCl.1 H$_2$O: C; 58.98%, H, 6.67%, N, 8.97%. Found: C; 58.71%, H; 6.97%, N, 8.72%.

Example 8

Preparation of (2S,3S)-3-(1-Isopropyl-6-methoxy-2-oxo-1,2,3,4-tetrahydroquinolin-7-yl)methylamino-2-phenylpiperidine dihydrochloride (Compound 33)

(i) 6-Methoxy-2-oxo-1,2,3,4-tetrahydroquinoline (Compound 29)

This compound was prepared according to the procedure (*J. Med. Chem* 30. 295(1987)).

(ii) 1-Isopropyl-6-methoxy-2-oxo-1,2,3,4-tetrahydroquinoline (Compound 30)

To a stirred solution of compound 29 (560 mg, 3.0 mmol) and 2-iodopropane (1.0 g, 6.0 mmol) in DMF (5 ml) was added NaH (240 mg, 6.0 mmol), and heated at 60 ° C. for 3 h. The mixture was diluted with water, extracted with $CH_2Cl_2$ (50 ml) three times. The combined extracts were dried over $Na_2SO_4$ and concentrated. The crude product was purified by a column chromatography on silicagel to give compound 30 (290 mg, 1.3 mmol, 44%) as a pale yellow crystal.

$^1$H—NMR (270 MHz) δ (CDCl$_3$) 7.10-6.70 (m, 3H), 4.68 (hep, 1H, J=7 Hz), 3.79 (s, 3H), 2.84-2.50 (m, 4H), 1.50 (d, 6H, J=7 Hz) ppm.

(iii) 1-Isopropyl-6-methoxy-2-oxo-1,2,3,4-tetrahydroquinoline-7-carboxaldehyde (Compound 31)

This compound was prepared from compound 30 in the same manner of compound 3

$^1$H-NMR (270 MHz) δ (CDCl$_3$) 10.43 (s, 1H), 7.57 (s, 1H), 6.82 (s, 1H), 4.67 (hep, 1H, J=7 Hz), 3.93 (s, 3H), 2.87 (t, 2H, J=7 Hz), 2.57 (t, 2H, J=7 Hz), 1.51 (d, 6H, J=7 Hz) ppm.

(iv) (2S,3S)-1-tert-Butoxycarbonyl-3-(1-isopropyl-6-methoxy-2-oxo-1,2,3,4-tetrahydroquinolin-7-yl) methylamino-2-phenylpiperidine (Compound 32)

This compound was prepared from compound 31 and compound 9 in the same manner of compound 11.

$^1$H—NMR (270 MHz) δ (CDCl$_3$) 7.65-6.60 (7H, m), 5.48 (1H, br), 4.62 (1H, hep, J=7 Hz), 4.03-3.75 (3H, m), 3.70 (3H, s), 3.14-2.48 (6H, m), 1.95-1.40 (4H, m), 1.48 (3H, d, J=7 Hz), 1.47 (3H, d, J=7 Hz), 1.40 (9H, s) ppm. This was employed in the next step without further purification.

(v) (2S,3S)-3-(1-Isoproply-6-methoxy-2-oxo-1,2,3,4-tetrahydroquinolin-7-yl)methylamino-2-phenylpiperidine dihydrochloride (Compound 33)

This compound was prepared from compound 32 in the same manner of compound 26.

mp 257–260° C. IR $v_{max}$ (KBr) 3440, 2960, 2925, 1665, 1554, 1506, 1464, 1455, 1435, 1412, 1372, 1355, 1326, 1316, 1234, 1196, 1141, 1033 cm$^{-1}$. $^1$H-NMR (270 MHz) δ (free base; CDCl$_3$) 7.40-6.50 (7H, m), 4.55 (1H, hep, J=7 Hz), 3.94-3.22 (4H, m), 3.49 (3H,s), 2.90-2.47 (6H, m), 2.20-1.38 (4H, m), 1.46 (3H, d, J=7 Hz), 1.46 (3H,, d, J=7 Hz) ppm. Anal. Calc for $C_{25}H_{33}N_3O_2$.2 HCl·H$_2$O: C; 60.24%, H, 7.48%, N, 8.43%. Found: C; 60.46%, H; 7.77%, N, 8.13%.

Example 9

Preparation of (2S,3S)-3-[(6-Difluoromethoxy- I -methyl-2-oxo-1,2,3,4-tetrahydroquinolin-7-yl)methyl]amino-2-phenylpiperidine dihydrochloride (Compound 37)

(i) 6-Hydroxy-1-methyl-2-oxo-1,2,3,4-tetrahydroquinoline-7-carboxaldehyde (Compound 34)

This compound was prepared from compound 16 in the same manner of compound 22.

$^1$H-NMR (270 MHz) δ (CDCl$_3$) 10.89 (1H, s), 9.88 (1H, s), 7.07 (1H. s), 6.85 (1H, s), 3.39 (3H, s), 2.98-2.88 (2H, m), 2.68-2.58 (2H, m) ppm.

(ii) 6-Difluoromethoxy-1-methyl-2-oxo-1,2,3,4-tetrahydroquinoline-7-carboxaldehyde (Compound 35)

To a stirred solution of compound 34 (160 m,, 0.78 mmol) and NaOH (200 mg, 5.0 mmol) in dioxane—H$_2$O (10 ml) was bubbled ClCHF$_2$ at 100° C. for 18 h. The solvent was removed by evaporation, and the residue was diluted with CH$_2$Cl$_2$. This was washed with water and brine, dried over MgSO$_4$, filtered, and concentrated. The crude product was purified by a column chromatography on silicagel to give compound 35 (20 mg, 0.078 mmol, 10%) as a white solid.

$^1$H-NMR (270 MHz) δ (CDCl$_3$) 10.34 (1H, s), 7.49 (1H, s), 7.11 (1H, s), 6.64 (1H, t, J=72.5 Hz), 3.40 (3H, s), 3.05-2.95 (2H, m), 2.73-2.63 (2H, m) ppm.

(iii) (2S,3S -1-tert-Butoxycarbonyl-3-[(6-difluoromethoxy-1-methyl-2-oxo-1,2,3,4-tetrahydroquinolin-7-yl)methyl]amino-2-phenylpiperidine (Compound 36)

This compound was prepared from compound 35 and compound 9 in the same manner of compound 11.

$^1$H-NMR (270 MHz) δ (CDCl$_3$) 7.62-7.53 (2H, m), 7.38-7.23 (3H, m), 6.95-6.91 (2H, m), 6.42 (1H, t, J 74.4 Hz), 5.52-5.43 (1H, m), 4.02-3.88 (3H, m), 3.29 (3H, s), 3.12-2.94 (2H, m), 2.90-2.82 (2H, m), 2.67-2.58 (2H, m), 2.00-1.40 (4H, m), 1.40 (9H, s) ppm.

(iv) (2S,3S)-3-[(6-Difluoromethoxy-1-methyl-2-oxo-1,2,3,4-tetrahydroquinolin-7-yl)methyl]amino-2-phenylpiperidine dihydrochloride (Compound 37)

This compound was prepared from compound 36 in the same manner of compound 26.

mp 238–240° C. IR ν$_{max}$ (KBr) 3440, 2930, 2763, 2475, 1681, 1521, 1431, 1116, 1044 cm$^{-1}$. $^1$H-NMR (270 MHz) δ (free base; CDCl$_3$) 7.42-7.22 (5H, m), 6.83 (1H, s), 6.75 (1H, s), 6.25 (1H, t, J=74.3 Hz), 4.03-3.98 (1H, m), 3.62 (1H, d, J=13.9 Hz), 3.42-3.33, (1H, m), 3.38 (1H, d, J=13.9 Hz), 3.19 (3H, s), 2.98-2.76 (4H, m), 2.65-2.55 (2H, m), 2.20-1.50 (4H, m) ppm. Anal. Calc for C$_{23}$H$_{27}$F$_2$N$_3$O$_2$.2 HCl: C; 56.56%, H, 5.98%, N, 8.60%. Found: C; 56.28%, H; 6.05%, N, 8.39%.

Example 10

Preparation of (2S,3S)-3-[[6-Methoxy-1-(2,2,2-trifluoroethyl)-2-oxo-1,2,3,4-tetrahydroquinolin-7-yl]methyl]amino-2-phenylpiperidinedihydrochloride (Compound 41)

(i) 6-Methoxy-1-(2,2,2-trifluoroethyl)-2-oxo-1,2,3,4-tetrahydroquinoline(Compound 38)

This compound was prepared from compound 29 and CH$_3$SO$_3$CH$_2$CF$_3$ in the same manner of compound 30.

$^1$H—NMR (270 MHz) δ (CDCl$_3$) 6.98 (1H, d, J=8.4 Hz), 6.80-6.72 (2H, m), 4.61 (2H, q, J=8.4 Hz), 3.80 (3H, s), 2.95 - 2.87 (2H, M), 2.75-2.67 (2H, m) ppm.

(ii) 6-Methoxy-1-(2,2,2-trifluoroethyl)-2-oxo-1,2,3,4-tetrahydroquinoline-7-carboxaldehyde (Compound 39)

This compound was prepared from compound 38 in the same manner of compound 3.

$^1$H-NMR (270 MHz) δ (CDCl$_3$) 10.43 (1H, s), 7.53 (1H, s), 6.86 (1H, s), 4.68 (2H, q, J=8.4 Hz), 3.95 (3H, s), 3.05-2.96 (2H, m), 2.78-2.69 (2H, m) ppm.

(iii) (2S,3S)-1-tert-Butoxycarbonyl-3-[[6-methoxy-1-(2,2,2-trifluoroethyl)-2-oxo-1,2,3,4-tetrahydroquinolin-7-yl]methyl]amino-2-phenylpiperidine (Compound 40)

This compound was prepared from compound 39 and compound 9 in the same manner of compound 11.

$^1$H-NMR (270 MHz) δ (CDCl$_3$) 7.60-7.50 (2H, m), 7.35-7.18 (3H, m). 6.98 (1H, s), 6.63 (1H, s), 5.53-5.38 (1H, m), 4.70-4.50 (2H, m), 3.98-3.70 (3H, m), 3.72 (3H, s), 3.08-2.80 (4H, m), 2.70-2.62 (2H, m), 1.90-1.40 (4H, m), 1.39 (9H, s) ppm.

(iv) (2S,3S)-3-[[6-Methoxy-1-(2,2,2-trifluoroethyl)-2-oxo-1,2,3,4-tetrahydroquinolin-7-yl]methyl]amino-2-phenylpiperidine dihydrochloride (Compound 41)

This compound was prepared from compound 40 in the same manner of compound 26.

mp 243–245° C. IR ν$_{max}$ (KBr) 3450, 2940, 2785, 2700, 1679, 1578, 1427, 1260, 1169, 1154, 1037 cm$^{-1}$. $^1$H-NMR (270 MHz) δ (free base; CDCl$_3$) 7.42-7.22 (5H, m), 6.87 (1H, s), 6.53 (1H, s), 4.82-4.48 (2H, m), 3.95 (1H, d, J=2.2 Hz), 3.65 (1H, J=14.3 Hz), 3.54 (3H, s), 3.41 (1H, d, J=14.3 Hz), 3.40-3.30 (1H, m), 2.95-2.80 (4H, m), 2.72-2.62 (2H, m), 2.20 -1.95 (2H, m), 1.73-1.45 (2H, m) ppm. Anal. Calc for C$_{24}$H$_{28}$F$_3$N$_3$O$_2$.2 HCl: C; 55.39%, H, 5.81%, N, 8.07%. Found: C; 55.05%, H; 5.87%, N, 8.08%.

Example 11

Preparation of (2S,3S)-3-[[1-Methyl-6-(2,2,2-trifluoroethoxy)-2-oxo-1,2,3,4-tetrahydroquinolin-7-yl]methyl]amino-2-phenylpiperidine dihydrochloride (Compound 45)

(i) 1-Methyl-6-(2,2,2-trifluoroethoxy)-2-oxo-1,2,3,4-tetrahydroquinoline(Compound 42)

This compound was prepared from compound 21 and CH$_3$SO$_3$CH$_2$CF$_3$ in the same manner of compound 23.

$^1$H-NMR (270 MHz) δ (CDCl$_3$) 6.95-6.78 (3H, m), 4.33 (2H, q, J=8.1 Hz), 3.34 (3H, s), 2.93-2.84 (2H, m), 2.68-2.59 (2H, m) ppm.

(ii) 1-Methyl-6-(2,2,2-trifluoroethoxy)-2-oxo-1,2,3,4-tetrahydroquinoline-7-carboxaldehyde (Compound 43)

This compound was prepared from compound 42 in the same manner of compound 3.

This was employed in the next step without further purification.

(iii) (2S,3)-1-tert-Butoxycarbonyl-3-[[1-methyl-6-(2.2.2-trifluoroethoxy)-2-oxo-1,2,3,4-tetrahydroquinolin-7-yl]methyl]amino-2-phenylpiperidine (Compound 44)

This compound was prepared from compound 43 and compound 9 in the same manner of compound 11.

$^1$H-NMR (270 MHz) δ (CDCl$_3$) 7.64-7.52 (2H, m), 7.36-7.22 (3H, m), 6.91 (1H, s), 6.63 (1H, s), 5.52-5.42 (1H, m), 4.29 (2H, q, J=8.4 Hz), 4.02-3.90 (1H, m), 3.93-3.78 (2H, m), 3.29 (3H, s), 3.12-2.88 (2H, m), 2.90-2.80 (2H, m), 2.67-2.57 (2H, m), 1.98-1.50 (4H, m), 1.40 (9H, s) ppm.

(iv) (2S,3S)-3-[[1-Methyl-6-(2,2,2-trifluoroethoxy)-2-oxo-1,2,3,4-tetrahydroquinolin-7-yl]methyl]amino-2-phenylpiperidine dihydrochloride (Compound 45)

This compound was prepared from compound 44 in the same manner of compound 26.

mp 239–240° C. IR ν$_{max}$ (KBr) 3440, 2955, 2775, 1650, 1520, 1471, 1454, 1292, 1245, 1158 cm$^{-1}$. $^1$H-NMR (270 MHz) δ (free base; CDCl$_3$) 7.38-7.20 (5H, m), 6.67 (1H, s), 6.55 (1H, s), 4.13 (2H, q, J=8.4 Hz), 3.95 (1H, d, J=1.8 Hz), 3.60 (1H, J=14.3 Hz), 3.41 (1H, d, J=14.3 Hz), 3.38-3.27 (1H, m), 3.19 (3H, s), 2.96-2.77 (4H, m), 2.65-2.57 (2H, m), 2.20-2.07 (1H, m). 2.00-1.37 (3H, m) ppm. Anal. Calc for C$_{24}$H$_{28}$F$_3$N$_3$O$_2$.2 HCl.2 H$_2$O: C; 51.80%, H, 6.16%, N, 7.55 %. Found: C; 51.45%, H; 5.91%, N, 7.38%.

Example 12

Preparation of(2S,3S)-3-[(6-Methoxy-1-methyl-2-thioxo-1,2,3,4-tetrahydroquinolin-7-yl)methyl]amino-2-phenylpiperidinedihydrochloride (Compound 49)

(i) 6-Methoxy-1-methyl-2-thioxo-1,2,3,4-tetrahydroquinoline (Compound 46)

To a stirred solution of compound 15 (350 mg, 1.83 mmol) in toluene (5 ml) was added Lawesson's Reagent (407 mg, 1.01 mmol), and refluxed for 1.5 h. The solvent was evaporated, and the residue was purified by a column chromatography on silicagel to give compound 46 (363 mg, 1.75 mmol, 96%) as a white solid.

$^1$H-NMR (270 MHz) δ (CDCl$_3$) 7.06 (1H, d, J=8.8 Hz), 6.79 (1H dd, J=8.8, 2.9 Hz), 6.72 (1H, d, J=2.9 Hz), 3.89 (3H, s), 3.81 (3H, s), 3.21-3.14 (2H, m), 2.81-2.74 (2H, m) ppm.

(ii) 6-Methoxy-1-methyl-2-thioxo-1,2,3,4-tetrahydroquinoline-7-carboxaldehyde (Compound 47)

This compound was prepared from compound 46 in the same manner of compound 3.

$^1$H-NMR (270 MHz) δ (CDCl$_3$) 10.44 (1H, s), 7.60 (1H, s), 6.83 (1H, s), 3.96 (3H, s), 3.92 (3H, s), 3.24-3.16 (2H, m), 2.91-2.83 (2H, m) ppm.

(iii) (2S,3S)-1-tert-Butoxycarbonyl-3-[(6-methoxy-1-methyl-2-thioxo-1,2,3,4-tetrahydroquinolin-7-yl)methyl]amino-2-phenylpiperidine (Compound 48)

This compound was prepared from compound 47 and compound 9 in the same manner of compound 11.

$^1$H-NMR (270 MHz) δ (CDCl$_3$) 7.60-7.53 (2H, m), 7.36-7.23 (3H, m). 7.04 (1H, s), 6.60 (1H, s), 5.53-5.45 (1H, m), 3.99-3.89 (1H, m), 3.85 (3H, s), 3.82 (2H, s), 3.73 (3H, s), 3.19-3.12 (2H, m), 3.11-2.92 (2H, m), 2.78-2.70 (2H, m), 1.90-1.50 (4H, m), 1.40 (9H, s) ppm.

(iv) (2S,3S)-3-[(6-Methoxy-1-methyl-2-thioxo-1,2,3,4-tetrahydroquinolin-7-yl)methyl]amino-2-phenylpiperidine dihydrochloride (Compound 49)

This compound was prepared from compound 48 in the same manner of compound 26.

mp 245–246° C. IR ν$_{max}$ (KBr) 3445, 2930, 2680, 1561, 1477, 1434, 1259, 1105 cm$^{-1}$. $^1$H—NMR (270 MHz) δ (free base; CDCl$_3$) 7.33-7.21 (5H, m), 6.82 (1H, s), 6.50 (1H, s), 3.92 (1H, d, J=2.2 Hz), 3.75 (3H, s), 3.66 (1H, d, J=13.9 Hz), 3.55 (3H, s), 3.43 (1H, d, J=13.9 Hz), 3.33-3.24 (1H, a)l 3.17-3.10 (2H. m), 2.88-2.67 (4H, m), 2.20-2.11 (1H, m), 2.03-1.80 (1H, m), 1.75-1.55 (1H, m), 1.54-1.42 (1H, m) ppm. Anal. Calc for C$_{23}$H$_{29}$N$_3$OS.2 HCl.0.1 H$_2$O: C; 58.46%, H, 6.88%, N, 8.82%. Found: C; 58.74%, H; 6.69%, N, 8.93%.

Example 13

Preparation of (2S,3S)-3-[(7-Methoxy-1-methyl-2-oxo-2,3,4,5-tetrahydro-1H-benzazepin-8-yl)methyl]amino-2-phenylpiperidine dihydrochloride (Compound 54)

(i) 7-Methoxy-2-oxo-2,3,4,5-tetrahydro-1H-benzazepine (Compound 50)

To a stirred solution of 6-methoxy-1-tetralone (1.0 g. 5.7 mmol) in CH$_2$Cl$_2$ (10 ml) was added conc. H$_2$SO$_4$ (5 ml) at 0° C., and then NaN$_3$(1.0 g) was added gradually over 30 min. The mixture was warmed up to room temperature, and stirred for 3h. The mixture was cooled, basified with NaOH aq., and extracted with CH$_2$Cl$_2$. The organic layers were combined, dried (MgSO$_4$), filtered, and concentrated, the residue was purified by a column chromatography on silicagel to give compound 50 (0.10 g, 0.52 mmol, 9.2%) as a white solid.

$^1$H-NMR (270 MHz) δ (CDCl$_3$) 7.65 (1H, br. s), 6.94-6.88 (1H, m) 6.78-6.68 (2H, m), 3.81 (3H, s), 2.77 (2H, t, J=7.0 Hz), 2.37-2.15 (4H, m) ppm.

(ii) 7-Methoxy-2-oxo-2,3,4,5-tetrahydro-1H-benzazepine-8-carboxaldehyde (Compound 51)

This compound was prepared from compound 50 in the same manner of compound 3.

This was employed in the next step without further purification.

(iii) 7-Methoxy-1-methyl-2-oxo-2,3,4,5-tetrahydro-1H-benzazepine-8-carboxaldehyde (Compound 52)

This compound was prepared from compound 51 in the same manner of compound 30.

$^1$H-NMR (270 MHz) δ (CDCl$_3$) 10.43 (1H, s), 7.63 (1H, s), 6.85 (1H, s), 3.97 (3H, s), 3.33 (3H, s), 2.82-2.74 (2H, m), 2.38-2.13 (4H, m) ppm.

(iv) (2S,3S)-1-tert-Butoxycarbonyl-3-[(7-methoxy-1-methyl-2-oxo-2,3,4,5-tetrahydro-1H-benzazepin-8-yl)methyl]amino-2-phenylpiperidine (Compound 53)

This compound was prepared from compound 52 and compound 9 in the same manner of compound 11.

$^1$H-NMR (270 MHz) δ (CDCl$_3$) 7.62-7.55 (2H, m), 7.38-7.22 (3H, m), 7.01 (1H, s), 6.60 (1H, s), 5.53-5.45 (1H, m), 4.00-3.72 (3H, m), 3.72 (3H, s). 3.27 (3H, s), 3.12-2.92 (2H, m), 2.70-2.60 (2H, m), 2.30-2.05 (4H, m), 1.92-1.40 (4H, m), 1.40 (9H, s) ppm.

(v) (2S,3S)-3-](7-Methoxy-1-methyl-2-oxo-2,3,4,5-tetrahydro-1H-benzazepin-8-yl)methyl]amino-2-phenylpiperidine dihydrochloride (Compound 54)

This compound was prepared from compound 53 in the same manner of compound 26.

mp 236–238° C. IR ν$_{max}$ (KBr) 3445, 2935, 2740, 1656, 1508, 1435, 1248, 1166 cm$^{-1}$. $^1$H-NMR (270 MHz) δ (free base; CDCl$_3$) 7.43-7.25 (5H, m), 6.82 (1H, s), 6.50 (1H, s), 4.12-4.08 (1H, m), 3.70 (1H, d, J=13.9 Hz), 3.58-3.43 (2H, m), 3.52 (3H, s), 3.22 (3H, s), 3.00-2.86 (2H, m), 2.68-2.58 (2H, m), 2.30-2.00 (6H, m), 1.75-1.54 (2H, m) ppm. Anal. Calc for C$_{24}$H$_{31}$N$_3$O$_2$.2 HCl.0.5 H$_2$O: C, 60.63%, H, 7.21%, N, 8.84%. Found: C, 60.95%, H, 7.11%. N, 8.87%.

Example 14

Preparation of (2S,3S)-3-[(7-Methoxy-1-methyl-2-oxo-1,2,3,4-tetrahydroquinolin-6-yl)methyl]amino-2-phenylpiperidine dihydrochloride (Compound 59)

(i) 7-Methoxy-2-oxo-1,2,3,4-tetrahydroquinoline (Compound 55)

This compound was prepared according to the procedure (*Chem. Pharm. Bull.*, 9, 970 (1961)).

(ii) 7-Methoxy-1-methyl-2-oxo-1,2,3,4-tetrahydroquinoline (Compound 56)

This compound was prepared from compound 55 in the same manner of compound 30.

$^1$H-NMR (270 MHz) δ (CDCl$_3$) 7.06 (1H, d, J=8.8 Hz), 6.57-6.48 (2H, m), 3.81 (3H, s), 3.33 (3H, s), 2.86-2.78 (2H, m), 2.68-2.58 (2H, at) ppm.

(iii) 7-Methoxy-1-methyl-2-oxo-1,2,3,4-tetrahydroquinoline-6-carboxaldehyde (Compound 57)

This compound was prepared from compound 56 in the same manner of compound 3.

$^1$H-NMR (270 MHz) δ (CDCl$_3$) 10.35 (1H, s), 7.65 (1H, s), 6.52 (1H, s), 3.96 (3H, s), 3.41 (3H, s), 2.93-2.85 (2H, m), 2.70-2.62 (2H, m) ppm.

(iv) (2S,3S)-1-tert-Butoxycarbonyl-3-[(7-methoxy-1-methyl-2-oxo-1,2,3,4-tetrahydroquinolin-6-yl)methyl]amino-2-phenylpiperidine (Compound 58)

This compound was prepared from compound 57 and compound 9 in the same manner of compound 11.

$^1$H-NMR (270 MHz) δ (CDCl$_3$) 7.62-7.55 (2H, m), 7.36-7.22 (3H, m), 6.97 (1H, s), 6.44 (1H, s), 5.53-5.46 (1H, m), 3.99-3.89 (1H, m), 3.85-3.69 (9H, m), 3.72 (3H, s), 3.35 (3H, s), 3.10-2.91 (2H, m), 2.84-2.76 (2H, m), 2.64-2.58 (2H, m), 1.88-1.52 (4H, m), 1.40 (9H, s) ppm.

(v) (2S,3S)-3-[(7-Methoxy-1-methyl-2-oxo-1,2,3,4-tetrahydroquinolin-6-yl)methyl]amino-2-phenylpiperidine dihydrochloride (Compound 59)

This compound was prepared from compound 58 in the same manner of compound 26.

mp 243–244° C. IR ν$_{max}$ 3450, 2940, 2785, 2700, 1679, 1578, 1427, 1260, 1169, 1154 cm$^{-1}$. $^1$H-NMR (270 MHz) δ (free base; CDCl$_3$) 7.38-7.23 (5H, m), 6.72 (1H, s), 6.32 (1H, s), 3.91 (1H, d, J=2.2 Hz), 3.61 (1H, d, J=13.6 Hz), 3.50 (3H, s), 3.39 (1H, d, J=13.6 Hz), 3.35-3.27 (1H, m), 3.32 (3H, s), 2.88-2.57 (6H, m), 2.20-2.12 (1H, m), 2.02-1.85 (1H, m), 1.70-1.55 (1H, m), 1.49-1.38 (1H, m) ppm. Anal. Calc for C$_{23}$H$_{29}$N$_3$O$_2$.2 HCl: C, 61.06%, H, 6.91%, N, 9.29%. Found: C, 60.67%, H, 6.97%, N, 9.57%.

Example 15

Preparation of (2S,3S)-3-[(7-Methoxy-1-methyl-2-oxo-4-trifluoromethyl-1,2,3,4-tetrahydroquinolin-6-yl)methyl]amino-2-phenylpiperidine dihydrochloride (Compound 65)

(i) 7-Methoxy-4-trifluoromethyl-2-quinolone (Compound 60)

This compound was prepared according to the procedure (J. Org. Chem., 45, 2285 (1980)).

(ii) 7-Methoxy-1-methyl-4-trifluoromethyl-2-quinolone (Compound 61)

This compound was prepared from compound 60 in the same manner of compound 30.

$^1$H—NMR (270 MHz) δ (CDCl$_3$) 7.82-7.75 (1H, m), 6.95-6.83 (3H, m), 3.94 (3H, s), 3.72 (3H, s) ppm.

(iii) 7-Methoxy-1-methyl-2-oxo-4-trifluoromethyl-1,2,3,4-tetrahydroquinoline (Compound 62)

The solution of 61 (200 mg, 0.78 mmol) in methanol (6 ml) was hydrogenated over 10% Pd-C (0.1 g) at atomospheric pressure for 22 houres. The catalyst was filtered off, and washed with methanol. The filtrate was concentrated to give 62 (190 mg, 0.75 mmol, 96%) as a white solid.

1H—NMR (270 MHz) δ (CDCl$_3$) 7.19 (1H, d, J=8.1 Hz), 6.65-6.58 (2H, m), 3.84 (3H, s), 3.60-3.42 (1H, m), 3.35 (3H, s), 3.07-2.83 (2H, m) ppm.

(iv) 7-Methoxy-1-methyl-2-oxo-4-trifluoromethyl-1,2,3,4-tetrahydroquinoline-6-carboxaldehyde (Compound 63)

This compound was prepared from compound 62 in the same manner of compound 3.

$^1$H-NMR (270 MHz) δ (CDCl$_3$) 10.35 (1H, s), 7.77 (1H, s), 6.58 (1H s), 4.00 (3H, s), 3.65-3.51 (1H, m), 3.43 (3H, s), 3.07 (1H, dd, J=16.9, 2.2 Hz), 2.91 (1H, dd, J=16.9, 7.3 Hz) ppm.

(v) (2S,3S)-1-tert-Butoxycarbonyl-3-[(7-methoxy-1-methyl-2-oxo-4-trifluoromethyl-1,2,3,4-tetrahydroquinolin-6-yl)methyl]amino-2-phenylpiperidine (Compound 64)

This compound was prepared from compound 63 and compound 9 in the same manner of compound 11.

$^1$H-NMR (270 MHz) δ (CDCl$_3$) 7.61-7.52 (2H, m), 7.36-7.22 (3H, m), 7.12 and 7.52 (total 1H, each s), 6.46 (1H, s), 5.52-5.42 (1H, m), 4.00-3.89 (1H, m), 3.88-3.71 (2H, m), 3.75 (3H, s), 3.52-3.37 (1H, m), 3.36 (3H, s), 3.09-2.76 (4H, m), 1.90-1.45 (4H, m), 1.40 (9H, s) ppm.

(vi) (2S,3S)-3-[(7-Methoxy-1-methyl-2-oxo-1,2,3,4-tetrahydroquinolin-6-yl)methyl]amino-2-phenylpiperidine dihydrochloride (Compound 65)

This compound was prepared from compound 64 in the same manner of compound 26.

mp 255–256° C. IR ν$_{max}$ (KBr) 3430, 2935, 2660, 1680, 1626, 1416, 1371, 1340, 1124, 1113 cm$^{-1}$. $^1$H—NMR (270 MHz) δ (free base; CDCl$_3$) 7.37-7.22 (5H, m), 6.81 and 6.78 (total 1H, each s), 6.36 and 6.31 (total 1H, each s), 3.93-3.88 (1H, m), 3.70-3.53 (4H, m), 3.46-3.24 (6H, m), 3.02-2.75 (4H, m), 2.17-2.05 (1H, m), 2.03-1.38 (3H, m) ppm. Anal. Calc for C$_{24}$H$_{28}$F$_3$N$_3$O$_2$.2 HCl: C, 55.39%, H, 5.81%, N, 8.07%. Found: C, 55.03%, H, 5.99%, N, 7.91%.

Example 16

Preparation of (2S,3S)-3-[(6-Methoxy-1-methyl-2-oxo-4H-3,1-benzoxazin-7-yl)methyl]amino-2-phenylpiperidine dihydrochloride (Compound 70)

(i) 6-Methoxy-4H-3,1-benzoxazin-2-one (Compound 66)

This compound was prepared according to the procedure (J. Med. Chem., 30, 95 (1987)).

(ii) 6-Methoxy-1-methyl-4H-3,1-benzoxazin-2-one (Compound 67)

This compound was prepared from compound 66 in the same manner of compound 30.

$^1$H-NMR (270 MHz) δ (CDCl$_3$) 6.90-6.83 (2H, m), 6.71-6.67 (1H, m), 5.16 (2H, s), 3.80 (3H, s), 3.35 (3H, s) ppm.

(iii) 6-Methoxy-1-methyl-2-oxo-4H-3,1-benzoxazine-7-carboxaldehyde (Compound 68)

This compound was prepared from compound 67 in the same manner of compound 3.

$^1$H-NMR (270 MHz) δ (CDCl$_3$) 10.46 (1H, s), 7.39 (1H, s), 6.81 (1H, s), 5.22 (2H, s), 3.94 (3H, s), 3.40 (3H, s) ppm.

(iv) (2S,3S)-1-tert-Butoxycarbonyl-3-[(6-methoxy-1-methyl-2-oxo-4H-3,1-benzoxazin-7-yl)methyl]amino-2-phenylpiperidine (Compound 69)

This compound was prepared from compound 68 and compound 9 in the same manner of compound 11.

$^1$H-NMR (270 MHz) δ (CDCl$_3$) 7.61-7.52 (2H, m), 7.35-7.22 (3H, m), 6.85 (1H, s), 6.57 (1H, s), 5.55-5.43 (1H, m), 5.14 (2H, s), 4.00-3.92 (1H, m), 3.91-3.87 (2H, m), 3.70 (3H, s), 3.32 (3H, s), 3.09-2.91 (2H, m), 1.92-1.50 (4H, m), 1.40 (9H, s) ppm.

(v) (2S,3S)-3-[(6-Methoxy-1-methyl-2-oxo-4H-3,1-benzoxazin-7-yl)methyl]amino-2-phenylpiperidine dihydrochloride (Compound 70)

This compound was prepared from compound 69 in the same manner of compound 26.

mp 235–237° C. IR ν$_{max}$ (KBr) 3420, 2935, 2665, 1728, 1564, 1508, 1481, 1429, 1302, 1037 cm$^{-1}$. $^1$H-NMR (270 MHz) δ (free base; CDCl$_3$) 7.35-7.20 (5H, m), 6.61 (1H, s), 6.47 (1H, s), 5.11 (2H, s), 3.90-3.87 (1H, m), 3.65 (1H, d, J=14.3 Hz), 3.53 (3H, s), 3.44 (1H, d, J=14.3 Hz), 3.30-3.18 (1H, m), 3.21 (3H, s), 2.86-2.74 (2H, m), 2.18-2.07 (1H, m), 1.98-1.38 (3H, m) ppm. Anal. Calc for C$_{22}$H$_{27}$N$_3$O$_3$.2 HCl: C, 58.15%, H, 6.43%, N, 9.25%. Found: C, 57.83%, H, 6.36%, N, 9.18%.

Example 17

Preparation of (2S,3S)-3-[(6-Methoxy-1-methyl-2-oxo-4H-3,1-benzothiazin-7-yl)methyl]amino2-phenylpiperidine dihydrochloride (Compound 75)

(i) 6-Methoxy-4H-3,1-benzothiazin-2-one (Compound 71)

This compound was prepared according to the procedure (J. Med. Chem., 30, 295 (1987)).

(ii) 6-Methoxy-1-methyl-4H-3,1-benzothiazin-2-one (Compound 72)

This compound was prepared from compound 71 in the same manner of compound 30.

$^1$H-NMR (270 MHz) δ (CDCl$_3$) 6.98 (1H, d, J=8.8 Hz), 6.84 (1H, dd, J=8.8, 2.9 Hz), 6.75 (1H, d, J=2.9 Hz), 3.93 (2H, s), 3.81 (3H, s), 3.42 (3H, s) ppm.

(iii) 6-Methoxy-1-methyl-2-oxo-4H-3,1-benzothiazine-7-carboxaldehyde (Compound 73)

This compound was prepared from compound 72 in the same manner of compound 3.

¹H-NMR (270 MHz) δ (CDCl₃) 10.45 (1H, s), 7.52 (1H, s), 6.86 (1H, s). 3.99 (2H, s), 3.96 (3H, s), 3.43 (3H, s) ppm.

(iv) (2S,3S)-1-tert-Butoxycarbonyl-3-[(6-methoxy-1-methyl-2-oxo-4H-3,1-benzothiazin-7-yl)methyl]amino-2-phenylpiperidine (Compound 74)

This compound was prepared from compound 73 and compound 9 in the same manner of compound 11.

¹H-NMR (270 MHz) δ (CDCl₃) 7.62-7.54 (2H, m), 7.37-7.22 (3H, m), 6.96 (1H, s), 6.62 (1H, s), 5.54-5.42 (1H, m), 4.02-3.90 (1H, m), 3.91 (2H, s). 3.82 (2H, s), 3.72 (3H, s), 3.38 (3H, s), 3.10-2.93 (2H, m), 1.93-1.50 (4H m). 1.40 (9H, s) ppm.

(v) (2S,3S)-3-[(6-Methoxy-1-methyl-2-oxo-4H-3,1-benzothiazin-7-yl)methyl]amino-2-phenylpiperidine dihydrochloride (Compound 75)

This compound was prepared from compound 74 in the same manner of compound 26.

mp 252–254° C. IR ν$_{max}$ (KBr) 3450, 2935, 2655, 1647, 1562, 1514, 1470, 1450, 1434, 1416, 1269, 1166, 1038 cm⁻¹. ¹H-NMR (270 MHz) δ (free base; CDCl₃) 7.36-7.19 (5H, m), 6.72 (1H, s), 6.52 (1H, s), 3.93-3.87 (3H, m), 3.64 (1H, d, J=14.3 Hz), 3.54 (3H, s), 3.43 (1H, d, J=14.3 Hz), 3.31-3.22 (1H, m), 3.28 (3H, s), 2.87-2.74 (2H, m), 2.18-2.07 (1H, m), 2.00-1.40 (3H, m) ppm. Anal. Calc for C₂₂H₂₇N₃O₂S.2 HCl: C, 56.17%, H, 6.21%, N, 8.93%. Found: C. 55.81%, H, 6.37%, N, 8.67%.

Example 18

Preparation of (2S,3S)-3-((7-Methoxy-4-methyl-3-oxo-3,4-dihydro-1,4-benzothiadin-6-yl)methyl)amino-2-phenylpiperidine dihydrochloride (Compound 79)

(i) 7-Methoxy-4-methyl-3-oxo-3,4-dihydro-1,4-benzothiadine (Compound 76)

This compound was prepared according to the procedure (*Indian J. Chem.* Sect B, 29B, 297(1990)).

(ii) 7-Methoxy-4-methyl-3-oxo-3,4-dihydro-1,4-benzothiadine-6-carboxaldehyde (Compound 77)

This compound was prepared from compound 76 in the same manner of compound 3.

¹H-NMR (270 MHz) δ (CDCl₃) 10.40 (1H, s), 7.53 (1H, s), 6.99 (1H, s), 3.93 (3H, s), 3.46 (2H, s), 3.45 (3H, s) ppm.

(iii) (2S,3S)-1-tert-Butoxycarbonyl-3-((7-methoxy-4-methyl-3-oxo-3,4-dihydro-1,4-benzothiadin-6-yl)methyl)amino-2-phenylpiperidine (Compound 78)

This compound was prepared from compound 77 and compound 9 in the same manner of compound 11.

¹H-NMR (270 MHz) δ (CDCl₃) 7.63-6.75 (7H, m), 5.48 (1H, br), 4.06-2.94 (14H, m), 1.95-1.20 (4H, m), 1.40 (9H, s) ppm.

This was employed in the next step without further purification.

(iv) (2S,3S)-3-((7-Methoxy-4-methyl-3-oxo-3,4-dihydro-1,4-benzothiadin-6-yl)methyl)amino-2-phenylpiperidine dihydrochloride (Compound 79)

This compound was prepared from compound 78 in the same manner of compound 26.

mp 263–269° C. ¹H-NMR (270 MHz) δ (free base; CDCl₃) 7.39-6.99 (7H, m), 3.92-2.75 (6H, m), 3.52 (3H, s), 3.36 (2H, s), 3.28 (3H, s), 2.20-1.40 (4H, m) ppm.

Example 19

Preparation of (2S,3S)-3-((7-Methoxy-4-methyl-3-oxo-3,4-dihydro-1,4-benzoxadin-6-yl)methyl)amino-2-phenylpiperidine dihydrochloride (Compound 83)

(i) 7-Methoxy4-methyl-3-oxo-3,4-dihydro-1,4-benzoxadine (Compound 80)

This compound was prepared according to the procedure (U.S. Pat. No. 4,552,956).

(ii) 7-Methoxy-4-methyl-3-oxo-3,4-dihydro-1,4-benzoxadine-6-carboxaldehyde (Compound 81)

This compound was prepared from compound 80 in the same manner of compound 3.

¹H-NMR (270 MHz) δ (CDCl₃) 10.35 (1H, s), 7.45 (1H, s), 6.62 (1H, s), 4.70 (2H, s), 3.91 (3H, s), 3.38 (3H, s) ppm.

(iii) (2S,3S)-1-tert-Butoxycarbonyl-3-((7-methoxy-4-methyl-3-oxo-3,4-dihydro-1,4-benzoxadin-6-yl)methyl)amino-2-phenylpiperidine (Compound 82)

This compound was prepared from compound 81 and compound 9 in the same manner of compound 11.

¹H-NMR (270 MHz) δ (CDCl₃) 7.63-6.49 (7H, m), 5.50 (1H, br), 4.56 (2H, s), 4.00-2.90 (6H, m), 3.67 (3H, s), 3.30 (3H, s), 1.90-1.30 (4H, m), 1.40 (9H, s) ppm.

This was employed in the next step without further purification.

(iv) (2S,3S)-3-((7-Methoxy-4-methyl-3-oxo-3,4-dihydro-1,4-benzoxadin-6-yl)methyl)amino-2-phenylpiperidine dihydrochloride (Compound 83)

This compound was prepared from compound 82 in the same manner of compound 26.

mp 263–267° C. ¹H-NMR (270 MHz) δ (free base; CDCl₃) 7.36-6.39 (7H, m), 4.55 (2H, s), 3.92-2.72 (6H, m), 3.49 (3H, s), 3.21 (3H, s), 2.20-1.37 (4H, m) ppm.

Example 20

Preparation of (2S,3S)-3-[(6-Methoxy-1,3,3-trimethyl-2-thioxo-2,3-dihydroindol-5-yl) methyl]amino-2-phenylpiperidine dihydrochloride (Compound 87)

(i) 6-Methoxy-1,3,3-trimethyl-2-thioxo-2,3-dihydroindol (Compound 84)

This compound was prepared from compound 2 in the same manner of compound 46.

¹H-NMR (270 MHz) δ (CDCl₃) 7.19 (1H, d, J=8.4 Hz), 6.72-6.55 (H, m), 3.85 (3H, s), 3.63 (3H, s), 1.41 (6H, s) ppm.

(ii) 6-Methoxy-1,3,3-trimethyl-2-thioxo-2,3-dihydroindol-5-carboxaldehyde (Compound 85)

This compound was prepared from compound 84 in the same manner of compound 3.

¹H-NMR (270 MHz) δ (CDCl₃) 10.42 (1H, s), 7.76 (1H, s), 6.60 (1H, s), 4.01 (3H, s), 3.68 (3H, s), 1.42 (6H, s) ppm.

(iii) (2S,3S)-1-tert-Butoxycarbonyl-3-[(6-methoxy-1,3,3-trimethyl-2-thioxo-2,3-dihydroindol-5-yl)methyl]amino-2-phenylpiperidine (Compound 86)

This compound was prepared from compound 85 and compound 9 in the same manner of compound 11.

¹H-NMR (270 MHz) δ (CDCl₃) 7.64-7.56 (2H, m), 7.37-7.22 (3H, m), 7.11 (1H, s), 6.51 (1H, s), 5.57-5.44 (1H, m), 3.98-3.70 (3H, m), 3.76 (3H, s), 3.64 (3H, s), 3.13-2.92 (2H, m), 1.90-1.40 (4H, m), 1.41 (9H, s), 1.38 (3H, s), 1.37 (3H, s) ppm.

(iv) (2S,3S)-3-[(6-Methoxy-1,3,3-trimethyl-2-thioxo-2,3-dihydroindol-5-yl)methyl]amino-2-phenylpiperidine dihydrochloride (Compound 87)

This compound was prepared from compound 86 in the same manner of compound 26.

mp 234–236° C. IR ν$_{max}$ (KBr) 3435, 2970, 2934, 2685, 1627, 1559, 1447, 1430, 1370, 1278, 1056 cm⁻¹. ¹H-NMR (270 MHz) δ (free base; CDCl₃) 7.37-7.23 (5H, m), 6.89 (1H, s), 6.40 (1H, s), 3.91 (1H, d, J=2.2 Hz), 3.67 (1H, d, J=13.9 Hz), 3.62 (3H, s), 3.57 (3H, s), 3.42 (1H, d, J=13.9

Hz), 3.33-3.22 (1H, m), 2.88-2.73 (2H, m), 2.19-1.35 (4H, m), 1.35 (3H, s), 1.34 (3H, s) ppm. Anal. Calc for $C_{24}H_{31}N_3OS.2$ HCl: C; 59.74%, H, 6.89%, N, 8.71%. Found: C; 60.02%, H; 6.91%, N, 8.64%.

Example 21
Preparation of(2S,3S)-3-[(7-Methoxy-1-methyl-2-thioxo-1,2,3,4-tetrahydroquinolin-6-yl) methyl]amino-2-phenylpiperidine dihydrochloride (Compound 91)

(i) 7-Methoxy-1-methyl-2-thioxo-1,2,3,4-tetrahydroquinolin (Compound 88)

This compound was prepared from compound 55 in the same manner of compound 46.

$^1$H-NMR (270 MHz) δ (CDCl$_3$) 7.08 (1H, d, J=8.1 Hz), 6.71 (1H, d, J=2.6 Hz), 6.64 (1H, dd, J=8.1, 2.6 Hz), 3.89 (3H, s), 3.83 (3H, s), 3.23-3.14 (2H, m), 2.78-2.68 (2H, m) ppm.

(ii) 7-Methoxy-1-methyl-2-thioxo-1,2,3,4-tetrahydroquinolin-6-carboxaldehyde (Compound 89)

This compound was prepared from compound 88 in the same manner of compound 3.

$^1$H-NMR (270 MHz) δ (CDCl$_3$) 10.37 (1H, s), 7.65 (1H, s), 6.69 (1H, s), 3.98 (3H, s), 3.95 (3H, s), 3.24-3.16 (2H, m), 2.82-2.74 (2H, m) ppm.

(iii) (2S,3S)-1-tert-Butoxycarbonyl-3-[(7-methoxy-1-methyl-2-thioxo-1,2,3,4-tetrahydroquinolin-6-yl)methyl]amino-2-phenylpiperidine (Compound 90)

This compound was prepared from compound 89 and compound 9 in the same manner of compound 11.

$^1$H-NMR (270 MHz) δ (CDCl$_3$) 7.60-7.53 (2H, m), 7.37-7.23 (3H, m), 6.99 (1H, s), 6.56 (1H, s), 5.53-5.43 (1H, m), 3.99-3.88 (1H, m), 3.90 (3H, s), 3.85-3.65 (2H, m), 3.73 (3H, s), 3.18-3.11 (2H, m), 3.10-2.90 (2H, m), 2.72-2.63 (2H, m), 1.90-1.50 (4H, m), 1.41 (9H, s) ppm.

(iv) (2S,3S)-3-[(7-Methoxy-1-methyl-2-thioxo-1,2,3,4-tetrahydroquinolin-6-yl) methyl]amino-2-2-phenylpiperidine dihydrochloride (Compound 91)

This compound was prepared from compound 90 in the same manner of compound 26.

mp. 219–221° C. IR ν$_{max}$ (KBr) 3435, 2940, 2660, 1626, 1558, 1464, 1430, 1416, 1369, 1338, 1103 cm$^{-1}$. $^1$H-NMR (270 MHz) δ (free base; CDCl$_3$) 7.42-7.23 (5H, m), 6.80 (1H, s), 6.45 (1H, s), 4.05-4.01 (1H, m), 3.87 (3H ,s). 3.66 (1H, d, J=13.9 Hz), 3.52 (3H, s), 3.50-3.40 (1H, m), 3.43 (1H, d, J=13.9 Hz), 3.18-3.10 (2H, m), 2.97-2.83 (2H, m), 2.68-2.58 (2H, m), 2.20-2.00 (2H, m), 1.80-1.50 (2H, m) ppm. Anal. Calc for $C_{23}H_{29}N_3OS.2HCl$. 0.5 H$_2$O: C; 57.85%, H, 6.75%, N. 8.80%. Found: C; 57.81%, H; 6.52%, N, 8.68%.

Example 22
Preparation of (2S,3S)-3-((1,6-Dimethoxy-2-oxo-1,2,3,4-tetrahydroquinolin-7-yl)methyl]amino-2-phenylpiperidine dihydrochloride (Compound 95)

(i) 1,6-Dimethoxy-2-oxo-1,2,3,4-tetrahydroquinoline (Compound 92)

This compound was prepared according to the procedure (*Terrahedron*, 43, 2577(1987)).

(ii) 1,6-Dimethoxy-2-oxo-1,2,3,4-tetrahydroquinoline-7-carboxaldehyde (Compound 93)

This compound was prepared from compound 92 in the same manner of compound 3.

(iii) (2S,3S)-1-tert-Butoxycarbonyl-3-((1,6-dimethoxy-2-oxo- 1,2,3.4-tetrahydroquinolin-7-yl)methyl)amino-2-phenylpiperidine (Compound 94)

This compound was prepared from compound 93 and compound 9 in the same manner of compound 11.

This was employed in the next step without further purification.

(v)(2S,3S)-3-((1,6-Dimethoxy-2-oxo-1,2,3,4-tetrahydroquinolin-7-yl)methyl)amino-2-phenylpiperidine dihydrochloride (Compound 95)

This compound was prepared from compound 94 in the same manner of compound 26.

Example 23

Preparation of (2S,3S)-3-[(1-Difluoromethyl-6-methoxy-2-oxo-1,2,3,4-tetrahydroquinolin-7-yl)methyl]amino-2-phenylpiperidine dihydrochloride (Compound 99)

(i) 6-Methoxy-2-oxo-1,2,3,4-tetrahydroquinoline-7-carboxaldehyde (Compound 96)

This compound was prepared from compound 29 in the same manner of compound 3.

$^1$H-NMR (270 MHz) δ (CDCl$_3$) 10.40 (s, 1H), 7.80 (br, 1H), 7.22 (s, 1H), 6.84 (s, 1H), 3.92 (s, 3H), 3.03 (t, 2H, J=7 Hz), 2.64 (t, 2H, J=7 Hz).

(ii) 1-Difluoromethyl-6-methoxy-2-oxo-1,2,3,4-tetrahydroquinoline-7-carboxaldehyde (Compound 97)

This compound was prepared from compound 96 and CF$_2$HCl in the same manner of compound 30.

$^1$H-NMR (270 MHz) δ (CDCl$_3$) 10.42 (s, 1H), 7.92 (s, 1H), 7.70 (t, 1H, J=59.7 Hz), 6.86 (s, 1H), 3.94 (s, 3H), 3.04-2.95 (m, 2H), 2.75-2.67 (m, 2H).

(iii) (2S,3S)-1-tert-Butoxycarbonyl-3-[(1-difluoromethyl-6-methoxy-2-oxo-1,2,3,4-tetrahydroquinolin-7-yl)methyl]amino-2-phenylpiperidine (Compound 98)

This compound was prepared from compound 97 and compound 9 in the same manner of compound 11.

$^1$H-NMR (270 MHz) δ (CDCl$_3$) 7.71 (t, 1H, J=60.1 Hz), 7.62-7.52 (m, 2H), 7.43 (s, 1H), 7.35-7.20 (m, 3H), 6.63 (s, 1H), 5.45-5.32 (m, 1H), 4.02-3.92 (m, 1H), 3.81 (s, 2H), 3.71 (s, 3H), 3.12-2.95 (m, 2H), 2.93-2.84 (m, 2H), 2.69-2.61 (m, 2H), 1.93-1.50 (m, 4H), 1.39 (s, 9H).

(iv) (2S,3S)-3-[(1-Difluoromethyl-6-methoxy-2-oxo-1,2,3,4-tetrahydroquinolin-7-yl)methyl]amino-2-phenylpiperidine dihydrochloride (Compound 99)

This compound was prepared from compound 98 in the same manner of compound 26.

$^1$H-NMR (270 MHz) δ (CDCl$_3$) 7.69 (t, 1H, J=60.1 Hz), 7.42-7.15 (m, 6H), 6.50 (s, 1H), 3.92 (d, 1H, J=1.8 Hz), 3.67-3.26 (m, 3H), 3.46 (s, 3H), 2.97-2.50 (m, 6H), 2.20-1.35 (m, 4H).

The chemical structures of the compounds prepared in Examples 1 to 23 are summarized in the following table.

TABLE

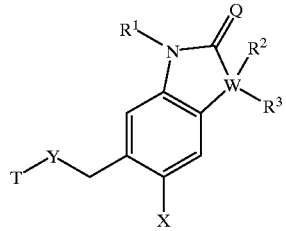

I(i)

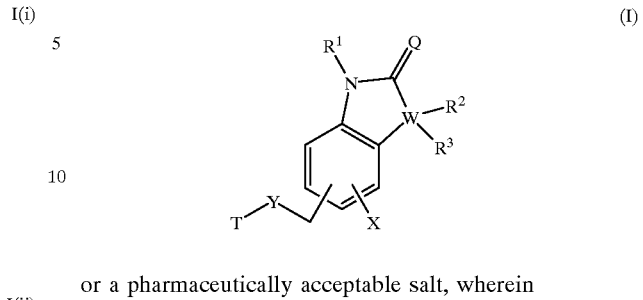

I(ii)

| Ex. # | formula | T | Y | X | —N(R$^1$)C(=Q)W(R$^2$)(R$^3$)— |
|---|---|---|---|---|---|
| 1 | I(ii) | q* | NH | OCH$_3$ | —N(CH$_3$)C(=O)C(CH$_3$)$_2$— |
| 2 | I(ii) | p* | NH | OCH$_3$ | —N(CH$_3$)C(=O)C(CH$_3$)$_2$— |
| 3 | I(i) | q | NH | OCH$_3$ | —N(CH$_3$)C(=O)CH$_2$CH$_2$— |
| 4 | I(i) | q | NH | OCH$_3$ | —N(CH$_3$)C(=O)CHCH— |
| 5 | I(i) | p | NH | OCH$_3$ | —N(CH$_3$)C(=O)CH$_2$CH$_2$— |
| 6 | I(i) | p | NH | OCH(CH$_3$)$_2$ | —N(CH$_3$)C(=O)CH$_2$CH$_2$— |
| 7 | I(i) | p | NH | OCH$_3$ | —N(CH$_3$)C(=O)CHCH— |
| 8 | I(i) | p | NH | OCH$_3$ | —N(CH(CH$_3$)$_2$)C(=O)CH$_2$CH$_2$— |
| 9 | I(i) | p | NH | OCH$_2$F$_3$ | —N(CH$_3$)C(=O)CH$_2$CH$_2$— |
| 10 | I(i) | p | NH | OCHF$_2$ | —N(CH$_2$CF$_3$)C(=O)CH$_2$CH$_2$— |
| 11 | I(i) | p | NH | OCH$_2$CF$_3$ | —N(CH$_3$)C(=O)CH$_2$CH$_2$— |
| 12 | I(i) | p | NH | OCH$_3$ | —N(CH$_3$)C(=S)CH$_2$CH$_2$— |
| 13 | I(i) | p | NH | OCH$_3$ | —N(CH$_3$)C(=O)CH$_2$CH$_2$CH$_2$— |
| 14 | I(ii) | p | NH | OCH$_3$ | —N(CH$_3$)C(=O)CH$_2$CH$_2$— |
| 15 | I(ii) | p | NH | OCH$_3$ | —N(CH$_3$)C(=O)CH$_2$CH(CF$_3$)— |
| 16 | I(i) | p | NH | OCH$_3$ | —N(CH$_3$)C(=O)OCH$_2$— |
| 17 | I(i) | p | NH | OCH$_3$ | —N(CH$_3$)C(=O)SCH$_2$— |
| 18 | I(i) | p | NH | OCH$_3$ | —N(CH$_3$)C(=O)CH$_2$S— |
| 19 | I(i) | p | NH | OCH$_3$ | —N(CH$_3$)C(=O)CH$_2$O— |
| 20 | I(ii) | p | NH | OCH$_3$ | —N(CH$_3$)C(=S)C(CH$_3$)$_2$— |
| 21 | I(ii) | p | NH | OCH$_3$ | —N(CH$_3$)C(=S)CH$_2$CH$_2$— |
| 22 | I(i) | p | NH | OCH$_3$ | —N(OCH$_3$)C(=O)CH$_2$CH$_2$— |
| 23 | I(i) | p | NH | OCH$_3$ | —N(CF$_2$H)C(=O)CH$_2$CH$_2$— |

*q: (2S,3S)-2-diphenylethylquinuclidin-3-yl, p: (2S,3S)-2-phenylpiperidin-3-yl

What is claimed is:

1. A compound of the formula (I)

or a pharmaceutically acceptable salt, wherein
W is ethylene;
R$^1$, R$^2$ and R$^3$ are independently hydrogen, C$_1$–C$_3$ alkyl, C$_1$–C$_3$ alkoxy or halo C$_1$–C$_3$ alkyl;
X is halo, C$_1$–C$_3$ alkyl, halo C$_1$–C$_3$ alkoxy or C$_1$–C$_3$ alkenyl;
Y is imino or oxy;
Q is oxygen or sulfur; and
T is (2S,3S)-2-phenylpiperidin-3-yl.

2. A compound according to claim 1, wherein X is C$_1$–C$_3$ alkoxy or halo C$_1$–C$_3$ alkoxy; Y is imino; and T is (2S,3S)-2-phenylpiperidin-3-yl.

3. A compound according to claim 2, wherein R$^1$ is methyl, isopropyl, methoxy or 2,2,2-trifluoroethyl; R$^2$ and R$^3$ are independently hydrogen, methyl or trifluoromethyl; and X is methoxy, isopropoxy, or difluoromethoxy.

4. A compound according to claim 3 selected from
(2S, 3S)-3-(6-methoxy-1-methyl-2-oxo-1,2,3,4-tetrahydroquinolin-7-yl)methylamino-2-phenylpiperidine;
(2S, 3S)-3-(1-isopropyl-6-methoxy-2-oxo-1,2,3,4-tetrahydroquinolin-7-yl)methylamino-2-phenylpiperidine;
(2S, 3S)-3-[(6-methoxy-1-methyl-2-thioxo-1,2,3,4-tetrahydroquinolin-7-yl)methyl]amino-2-phenylpiperidine dihydrochloride;
(2S, 3S)-3-[(7-methoxy-1-methyl-2-oxo-1,2,3,4-tetrahydroquinolin-6-yl)methyl]amino-2-phenylpiperidine dihydrochloride.

5. A compound according to claim 3 selected from
(2S, 3S)-3-[(6-methoxy-1-methyl-2-thioxo-1,2,3,4-tetrahydroquinolin-7-yl)methyl]amino-2-phenylpiperidine dihydrochloride.

6. A pharmaceutical composition for treating a mammal requiring inhibition of the biological action of Substance P which comprises a therapeutically effective amount of a compound of claim 1 together with a pharmaceutically acceptable carrier.

* * * * *